United States Patent
Luyten et al.

(10) Patent No.: US 7,482,114 B2
(45) Date of Patent: *Jan. 27, 2009

(54) IN VIVO ASSAY AND MOLECULAR MARKERS FOR TESTING THE PHENOTYPIC STABILITY OF CELL POPULATIONS, AND SELECTED CELL POPULATIONS FOR AUTOLOGOUS TRANSPLANTATION

(75) Inventors: Frank Luyten, Kraainem (BE); Cosimo De Bari, Leuven (BE); Francesco Dell'Accio, Heverlee (BE)

(73) Assignee: Tigenix N.V., Leuven (BE)

( * ) Notice: Subject to any disclaimer, the term of this patent is extended or adjusted under 35 U.S.C. 154(b) by 785 days.

This patent is subject to a terminal disclaimer.

(21) Appl. No.: 10/422,475

(22) Filed: Apr. 24, 2003

(65) Prior Publication Data

US 2003/0235813 A1 Dec. 25, 2003

Related U.S. Application Data

(63) Continuation-in-part of application No. 10/089,932, filed as application No. PCT/BE00/00118 on Oct. 6, 2000.

(60) Provisional application No. 60/375,218, filed on Apr. 24, 2002.

(30) Foreign Application Priority Data

Oct. 6, 1999 (EP) .................................. 99203273

(51) Int. Cl.
*C12Q 1/00* (2006.01)
(52) U.S. Cl. ........................................................ 435/4
(58) Field of Classification Search .................... 435/4, 435/29, 15, 23, 7.1, 975; 530/300
See application file for complete search history.

(56) References Cited

U.S. PATENT DOCUMENTS

| 5,723,331 | A | | 3/1998 | Tubo | |
|---|---|---|---|---|---|
| 5,837,258 | A | * | 11/1998 | Grotendorst | 424/198.1 |
| 5,902,785 | A | | 5/1999 | Hattersley | |

FOREIGN PATENT DOCUMENTS

| WO | WO 96/41620 | | 12/1996 |
|---|---|---|---|
| WO | WO 98/05903 | | 12/1998 |
| WO | WO 01/24833 | * | 4/2001 |
| WO | WO 01/24833 A2 | | 4/2001 |
| WO | WO 01/25402 A1 | | 4/2001 |

OTHER PUBLICATIONS

Schumacher et al, J. Orthopaedic Research, V. 17(1), pp. 110-120, (1999) Abstract Only.*
Kolettas et al, "Expression of cartilage-specific molecules is retained on long-term culture of human articular chondrocytes," (Journal of Cell Science), 1995, vol. 108, pp. 1991-1999.*
Si et al, "Eexpression of BMP-2 and TGF-beta 1 mRNA during healing of the rabbit mandible," (Eur. J. of Oral Science), Aug. 1997, vol. 105, No. 4, Abstract only.*
Hamada et al, "Immunohistochemical localization of fibroblast growth factor receptors in the rat mandibular condylar cartilage and tibial cartilage," (J. of Bone and Mineral Metab.), 1999, vol. 17, pp. 274-282.*
Meyer et al, "Mapping the Type I Collagen-binding Site on Pigment Epithelium-derived Factor," (The J. of Biol. Chem.), Nov. 2002, vol. 277, No. 47, pp. 45400-45407.*
Quan et al, "Localization of Pigment Epiothelium-Derived Factor in Growing Mouse Bone," (Calcif. Tissue Int.), 2005, vol. 76, pp. 146-153.*
Quarto et al, "Modulation of Commitment, Proliferation, and Differentiation of Chondrogenic Cells in Defined Culture Medium," (Endocrinology), 1997, vol. 138, No. 11, pp. 4966-4976.*
Binette et al, "Expression of a Stable Articular Cartilage Phenotype without Evidence of Hypetrophy by Adult Human Articular Chondrocytes In Vitro," (Journal of Orthopaedic Research), vol. 16, No. 2, p. 207-216.*
Rousseau et al, "Mutations in the gene encoding fibroblast growth factor receptor-3 in achondroplasia," (Nature), vol. 371, Sep. 15, 1994, pp. 252-254.*
U.S. Appl. No. 10/089,932, Frank Luyten.
Bradham et al., "In Vivo Cartilage Formation From Growth Factor Modulated Articular Chondrocytes," Clin. Orthop. Rel. Res., 352: 239-249, (1998).
Erlacher et al., "Cartilage-Derived Morphogenetic Proteins and Osteogenic Protein-1 Differentially Regulate Osteogenesis." J. Bone Miner. Res. 13:383-392, (1998).
Stewart et al., "Phenotypic Stability of Articular Chondrocytes In Vitro: The Effects of Culture Models, Bone Morphogenetic . . . " J. Bone Min 15(1):166-74 (2000) (abstract).
Valcourt et al., "Different Effects of Bone Morphogenetic Proteins 2, 4, 12, and 13 on the Expression of Cartilage and Bone Markers . . . " Exp. Cell Res. 251:264-274 (1999).
Office Action for U.S. Appl. No. 10/089,932 (Dated Oct. 5, 2004).
Office Action for U.S. Appl. No. 10/089,932 (Dated Apr. 21, 2006).
Office Action for U.S. Appl. No. 10/089,932 (Dated Oct. 24, 2006).
Office Action for U.S. Appl. No. 10/089,932 (Dated Apr. 19, 2007).
Advisory Action for U.S. Appl. No. 10/089,932 (Dated Jul. 2, 2007).
Office Action for U.S. Appl. No. 10/089,932 (Dated Jan. 14, 2008).

* cited by examiner

*Primary Examiner*—Ralph Gitomer
*Assistant Examiner*—Amanda P Wood
(74) *Attorney, Agent, or Firm*—Clark & Elbing LLP

(57) ABSTRACT

An in vivo assay to measure anchorage-independent growth and phenotypic stability of a certain cell population comprising subcutaneous or intramuscular injection in a mammal of a cell suspension of articular chondrocytes in an iso-osmotic liquid, the same suspension comprising articular chondrocytes in an amount equivalent to at least $1 \times 10^6$ chondrocytes as applied to immune-deficient mice. The outcome is linked to molecular markers. The present invention further relates to DNA chips and diagnostic tools comprising the latter to predict the outcome of ACT. Antibodies raised against positive and negative markers of chondrocyte stability can also be used for quality control on the chondrocytes. Therapeutical compositions comprising stable chondrocytes are very useful for tissue repair.

17 Claims, 6 Drawing Sheets

IN VIVO ASSAY AND MOLECULAR MARKERS FOR TESTING THE PHENOTYPIC STABILITY OF CELL POPULATIONS, AND SELECTED CELL POPULATIONS FOR AUTOLOGOUS TRANSPLANTATION

RELATED APPLICATIONS

This application is a continuation-in-part of copending U.S. patent application Ser. No. 10/089,932 filed Jul. 29, 2002 which is the national filing of international application number PCT/BE00/00118 filed Oct. 6, 2000. The present application is also the non-provisional filing of provisional application No. 60/375,218, filed Apr. 24, 2002.

The present invention relates to the field of cartilage repair in general, and more specifically to the generation of an optimal cell population suitable for the repair of joint surface defects and the repair of the cartilage skeleton in general.

BACKGROUND OF THE INVENTION

Cartilage is a tissue composed by a cellular component, chondrocytes, and by an extra-cellular matrix typically rich in collagen type II and highly sulphated high molecular weight proteoglycan aggregates. The latter property confers cartilage its peculiar histochemical characteristics that are: strong staining with Alcian blue at low pH (from 0.2 to 2.5) and metachromacy with Toluidine blue and Safranin O. The abundance of type II collagen, link protein, and proteoglycan aggrecan, along with the presence of minor collagens such as type IX and type XI collagen are hallmarks of cartilage tissue.

In post-natal mammals, cartilage contributes to the structure of several organs and systems like the articular surface of diarthrodial joints and other joint-associated structures (such as menisci), the ear, the nose, the larynx, the trachea, the bronchi, structures of the heart valves, part of the costae, synchondroses, entheses etc. In some of the mentioned locations (e.g. entheses, the annulus fibrosus of the intervertebral disks, in the menisci, insertion of ligaments etc.) for the abundance of collagens (mostly type I collagen) and the peculiar distribution of the fibrous bundles it is called fibrocartilage. In other locations (e.g. the pinna of the ear, epiglottis etc.) it is particularly rich in elastin and it is called elastic cartilage. In all the other structures, for its semi-transparent, clear aspect it is called hyaline cartilage.

During embryogenesis cartilage has a role in the development of long bones. Mesenchymal cells aggregate and differentiate to form cartilage anlagen, which provide the mold of the future long bones. These cartilage templates in development evolve, undergo endochondral bone formation through a cascade of events including chondrocyte hypertrophy, vascular invasion, mineralization, and are eventually replaced by bone except for a thin layer at the extremities of the bone elements that will differentiate into the articular surface of diarthrodial joints. In these locations cartilage tissue remains hyaline for all the life-span of the individual. With ageing, articular cartilage is well known to undergo a process of senescence, affecting its mechanical properties and its intrinsic resilience.

Joint surface defects can be the result of various aetiologies such as inflammatory processes, neoplasias, post-traumatic and degenerative events etc. Whatever the cause, the mechanisms of repair and of subsequent evolution are largely common.

Osteochondral (or full-thickness) articular surface defects include damage to the articular cartilage, the underlying subchondral bone tissue, and the calcified layer of cartilage located between the articular cartilage and the subchondral bone. They typically arise during severe trauma of the joint or during the late stages of degenerative joint diseases, e.g. during osteoarthritis. These lesions disrupt the congruence between the joint surfaces and therefore can lead to OA, which can be painful and severely limit the joint function. Osteochondral defects can rely on an extrinsic mechanism for repair. Extrinsic healing uses mesenchymal elements from subchondral bone to participate in the formation of new connective tissue. The repair tissue, however, often consists of fibrocartilage or fibrous tissue. This scar tissue does not share the same biomechanical properties as hyaline cartilage and eventually degenerates with the development of osteoarthritis.

Superficial or partial-thickness injuries of the articular cartilage that do not penetrate the subchondral bone can only rely on an intrinsic mechanism for repair. Chondrocytes adjacent to the injured surfaces proliferate and increase the deposition of extracellular matrix. Despite these attempts at repair, there is no appreciable increase in the bulk of cartilage matrix and the repair process is rarely effective in healing the defects. Although initially sometimes painless, partial-thickness defects often degenerate into osteoarthritis of the involved joint.

Repair of articular cartilage defects with suspensions of chondrocytes has been carried out in a variety of animal models (Brittberg et al. (1996) Clin. Orthop. (326):270-83) and is now employed in humans (Brittberg et al. N Engl J Med. 1994 Oct. 6; 331(14):889-95). Autologous chondrocytes obtained from an unaffected area of the joint are released, expanded in vitro in the presence of autologous serum and subsequently injected under a periosteal flap sutured to cover the cartilage defect. This procedure has led to a proven at least symptomatic amelioration. This conceptually promising approach has still wide margins for improvement, since it is known that in vitro expansion of chondrocytes results, after a limited number of cell divisions, in a loss of their phenotypic stability (as defined by the ability of chondrocytes to form hyaline cartilage in vivo) making the cell suspension to be injected unreliable.

Three alternative approaches have been developed in an attempt to improve the success rate in treating mammalian articular cartilage defects. In the first approach, synthetic carrier matrices are impregnated with allogeneic chondrocytes and then implanted into the cartilage defect where they hopefully produce and secrete components of the extracellular matrix to form articular cartilage at the site of the defect. A variety of synthetic carrier matrices have been used to date and include three-dimensional collagen gels (e.g. U.S. Pat. No. 4,846,835), reconstituted fibrin-thrombin gels (e.g. U.S. Pat. Nos. 4,642,120; 5,053,050 and 4,904,259), synthetic polymer matrices containing polyanhydride, polyorthoester, polyglycolic acid and copolymers thereof (U.S. Pat. No. 5,041,138), and hyaluronic acid-based polymers. Once a mitotically expanded population of chondrocytes is obtained, the cells can be implanted either back into the same subject from which their parent cells were originally derived (autologous implantation), or into a different subject (heterologous implantation). In addition, heterologous implantation may use chondrocytes obtained from a related or unrelated individual of the same species (allogeneic), or from a different species (xenogeneic). Alternatively, chondrocytes may be obtained from an established, long-term cell line that is either allogeneic or xenogeneic.

The introduction of non-autologous materials into a patient, however, may stimulate an undesirable immune response directed against the implanted material, leading to potential rejection of the newly-formed and engrafted cartilage tissue. In addition, heterologous implantation risks the transmission to the subject of infectious agent(s) present in the tissue or cell line. Neo-cartilage may be formed around the periphery of the implant thereby preventing integration of the implant into the cartilage defect. Monitoring the formation and development of the resulting synthetic cartilage in situ is difficult to perform and usually involves an arthroscopic or open joint examination. Furthermore, implants containing synthetic polymer components may be unsuitable for repairing large cartilage defects since polymer hydrolysis in situ inhibits the formation of cartilage and/or its integration into the defect.

In the second approach, the defect is filled with a biocompatible, biodegradable matrix containing chemotactic and mitogenic growth factors to stimulate the influx of chondrocyte progenitor cells into the matrix in situ. The matrices optimally contain pores of sufficient dimensions to permit the influx into, and proliferation of the chondrocyte progenitor within the matrix. The matrix also may contain differentiating growth factors to stimulate the differentiation of chondrocyte progenitor cells into chondrocytes which in turn hopefully secrete extracellular matrix components to form cartilage at the site of the defect in situ (e.g. U.S. Pat. Nos. 5,206,023 and 5,270,300 and EP-A-530,804). This approach however results in problems similar to those associated with the first approach hereinabove. Furthermore there is no data so far that articular cartilage contains chondrocytic progenitors available for partial thickness defect repair.

In the third approach, chondrocytes may be cultured and expanded in vitro thereby to form synthetic cartilage-like material that is implanted subsequently into the cartilage defect. This has the advantage over the previous methods in that the development of the synthetic cartilage material may be monitored, through morphological, biochemical, and molecular characterisation, prior to implantation. Chondrogenic cells may be expanded in either an anchorage-dependent or an anchorage-independent culture system. In the latter, chondrogenic cells may be cultured as colonies within an agarose gel. Heretofore, only small pieces of cartilage tissue of undefined shape have been prepared using this manner. Furthermore, the resulting cartilage remains embedded within a gel matrix making it less suitable for implantation into mammals. Alternatively, in another anchorage-independent method, chondrocytes may be cultured as colonies in suspension culture. However the resulting particles containing synthetic cartilage-like material are usually small and of undefined shape, and do not integrate with each other and with the surrounding cartilage within the defect. This makes them unsuitable for implantation and repair of a predetermined articular cartilage defect.

In the anchorage-dependent method, primary cultures of chondrogenic cells isolated from primary tissue are grown as monolayer attached to the surface of a cell culture flask (e.g. U.S. Pat. No. 4,356,261). The primary cells derived directly from explant tissue remain capable of producing and secreting extracellular components characteristic of natural cartilage, specifically type II collagen and sulphated proteoglycans. However, it is well known that during in vitro expansion as monolayers, chondrocytes dedifferentiate and lose their ability to form hyaline cartilage in vivo. Until now it has not been possible to prepare large patches of articular cartilage from small pieces of biopsy tissue using the anchorage-dependent procedures of U.S. Pat. No. 4,356,261.

In order to solve the above problems, U.S. Pat. No. 5,723,331 provides a method for preparing in vitro large quantities of synthetic cartilage from small samples of biopsy tissue which, based on the discovery that chondrogenic cells may be isolated from a variety of tissues, e.g. pre-existing cartilage, perichondrial tissue or bone marrow, and expanded in vitro prior to cartilage formation, includes first seeding denuded (i.e. isolated from an enzymatically or mechanically disaggregated tissue) chondrogenic cells, proliferated ex vivo, into a pre-shaped well having a cell contacting, cell adhesive surface, and then culturing the proliferated chondrogenic cells in the well for a time sufficient to permit the cells to secrete an extracellular matrix thereby to form a three-dimensional, multi cell-layered patch of synthetic cartilage. This approach does not yield an optimal integration between the implant and the surrounding cartilage. Thus far there is no evidence on the phenotypic stability of cells in such preparations.

The use of mesenchymal cells has also been proposed for cartilage repair. Mesenchymal cells are a potential alternative source of cartilage-producing cells. They are generally recognised as pluripotent cells capable of dividing many times to produce progeny cells that can eventually give rise to many tissues, including skeletal tissues such as cartilage, bone, tendon, ligament, marrow stroma and connective tissue. By definition, they can undergo many more divisions. Chondro/osteoprogenitor cells, which are bipotent with the ability to differentiate into cartilage or bone, were isolated from bone marrow (e.g. in U.S. Pat. No. 5,226,914), and subsequently from muscle, heart and granulation tissue. Pluripotency is demonstrated using different culture conditions and adding more or less specific inducers, which elicit differentiation of the stem cells into chondrocytes (cartilage), osteoblasts (bone), myotubes (muscle), adipocytes (fat).

It would be highly desirable to have progenitor cells which are easily obtained such as by muscle biopsy, cultured to yield large numbers, and can be used as a source of chondrocytes or osteoblasts or myocytes. However, the same pluripotency that makes them attractive, conveys the risk of metaplastic differentiation. In other words there is the risk that they could differentiate in an undesired direction (e.g. bone or fat within a cartilage defect). In U.S. Pat. Nos. 5,226,914 and 5,197,985 the cells were absorbed into porous ceramic blocks and implanted, yielded primarily bone. However, U.S. Pat. No. 5,906,934 discloses that under very specific conditions mesenchymal stem cells in a suitable polymeric carrier (such as polyglycolic acid mesh) implanted into a cartilage and/or bone defect will differentiate to form cartilage and/or bone, as appropriate. Also U.S. Pat. No. 5,919,702 discloses chondrocyte progenitor cells isolated from umbilical cord sources, e.g. from Wharton's jelly, and cultured so as to give rise to chondrocytes that can produce cartilage tissue. Also in another attempt to avoid the drawbacks of current cartilage and bone repair techniques which cause bleeding and involve the use of mechanically weak non self-derived material, U.S. Pat. No. 5,866,415 suggests treating cartilage or bone defects with a biological material obtained by attaching in vitro cartilage or bone forming cells to a periosteum of sufficient size to accommodate the defect.

WO/96/41523 and WO96/41620 describe the use of FGFR3 as a marker for mesenchymal skeletal progenitor cells. Such cells do not show a stable phenotype. To initiate differentiation of these cells factors may be added to the cells or in situ, for example an FGF9 antagonist. As indicated above the use of progenitor cells for implantation in the body is counter-indicated due to the danger of metaplastic differentiation.

Transforming growth factor-beta ("TGF-β") refers to a family of related dimeric proteins which regulate the growth and differentiation of many cell types. Members of this family include TGF-β1, TGF-β2, TGF-β3, TGF-β4, TGF-β5, morphogenic proteins ("MP") such as MP-121 and MP-52, inhibins/activins (such as disclosed in EP-A-222,491), osteogenic proteins ("OP"), bone morphogenetic proteins (hereinafter denoted "BMP"), growth/differentiation factors ("GDF") such as GDF-1, GDF-3, GDF-9 and Nodal. TGF-β was first characterised for its effects on cell proliferation. It both stimulated the anchorage-independent growth of rat kidney fibroblasts and inhibited the growth of monkey kidney cells. TGF-β family members have been shown to have many diverse biological effects, e.g. they regulate bone formation, induce rat muscle cells to produce cartilage-specific macromolecules, inhibit the growth of early haematopoietic progenitor cells, T cells, B cells, mouse keratinocytes, and several human cancer cell lines. TGF-β family members increase the synthesis and secretion of collagen and fibronectin, accelerate healing of incisional wounds, suppress casein synthesis in mouse mammary explants, inhibit DNA synthesis in rat liver epithelial cells, stimulate the production of bFGF binding proteoglycans, modulate phosphorylation of the epidermal growth factor ("EGF") receptor and proliferation of epidermoid carcinoma cells and can lead to apoptosis in uterine epithelial cells, cultured hepatocytes and regressing liver. TGF-β's can mediate cardio-protection against reperfusion injury by inhibiting neutrophil adherence to endothelium and protect against experimental autoimmune diseases in mice. On the whole, proteins of the TGF-β family are multifunctional, active growth factors and also have related biological activities such as chemotactic attraction of cells, promotion of cell differentiation and tissue-inducing capabilities. Differences in their structure and in their affinity for receptors lead to considerable variations in their exact biological function.

In contrast to the foregoing reports of the ability of TGF-β to induce the production of cartilage-specific macromolecules in muscle cells and chondrocytes, TGF-β was found to act synergistically with fibroblast growth factor to inhibit the synthesis of collagen type II by chicken sternal chondrocytes and in rat chondrocytes. In fact, TGF-β, has emerged as the prototypical inhibitor of the proliferation of most normal cell types in vitro as well as in vivo, exhibiting a remarkable diversity of biological activity. TGF-β1 has been purified from human and porcine blood platelets and recombinant TGF-β1 is currently available.

Among the sub-family of BMPs, the structures of BMP-1 through BMP-15 have previously been elucidated. The unique inductive activities of these proteins, along with their presence in bone, suggests that they are important regulators of bone repair processes and may be involved in the normal maintenance of bone tissue. Recently, the BMP-12-related subfamily of proteins, including BMP-13 and MP52 (see e.g. WO93/16099 and U.S. Pat. No. 5,658,882), was shown to be useful in compositions for the induction of tendon/ligament-like tissue formation and repair. U.S. Pat. No. 5,902,785 discloses that BMP-12 related proteins are particularly effective for the induction of cartilaginous tissue and that BMP-9 is useful for increasing proteoglycan matrix synthesis and therefore for the maintenance of cartilaginous tissue. It also describes compositions comprising a BMP-12 related protein and additionally including one or more TGF-β superfamily member proven to be osteogenic, preferably BMP-2, -4, -5, -6 and/or BMP-7 as useful for the regeneration of multiple tissue types (for example at the interface or junction between tissues) and especially useful for the treatment of articular cartilage, in which the articular surface, cartilage, subchondral bone and/or tidemark interface between cartilage and bone need to be repaired. The same patent further describes compositions comprising a BMP-12 related protein together with a protein useful for the maintenance of chondrocytes or cartilaginous tissue such as BMP-9, the said compositions being especially useful for the induction and maintenance of cartilaginous tissue at a site in need of cartilage repair such as an articular cartilage defect.

WO96/14335 discloses, using mRNA prepared from newborn articular cartilage, the isolation of two members of the BMP family, designated Cartilage-derived morphogenetic proteins-1 and -2 (CDMP-1, CDMP-2). Storm et al. (1994) in Nature 368, 639-43 and Chang et al. (1994) in J.Biol.Chem. 269, 28227-34 independently established that CDMP-1 mapped close to the brachypodism locus on chromosome 2 in mice and might be involved in the brachypodism phenotype. Also the expression patterns of CDMP's suggests an important role for these genes in joint morphogenesis. WO98/59035 also discloses a method of maintaining a cartilaginous phenotype in chondrocytes in vitro, comprising culturing the chondrocytes in serum-free medium containing a CDMP and/or BMP.

Table 1 summarises the BMP subfamily members according to Reddi A H, Nature Biotechnol. 1998, 16:247-52.

TABLE 1

The BMP family in mammals

| BMP subfamily | Generic name | BMP designation |
|---|---|---|
| BMP 2/4 | BMP-2A | BMP-2 |
|  | BMP-2B | BMP-4 |
| BMP 3 | Osteogenin | BMP-3 |
|  | Growth/differentiation factor 10 | BMP-3B |
| Op-1/BMP-7 | BMP-5 | BMP-5 |
|  | Vegetal related-1 (Vgr-1) | BMP-6 |
|  | Osteogenic Protein-1 (Op-1) | BMP-7 |
|  | Osteogenic Protein-2 (Op-2) | BMP-8 |
|  | Osteogenic Protein-3 (Op-3) | BMP-8B |
|  | Growth/differentiation factor 2 (GDF-2) | BMP-9 |
|  | BMP-10 | BMP-10 |
|  | Growth/differentiation factor 11 (GDF-11) | BMP-11 |
| GDF-5, 6, 7 | Growth/differentiation factor 7 (GDF-7) or cartilage-derived morphogenic protein-3 (CDMP-3) | BMP-12 |
|  | Growth/differentiation factor 6 (GDF-6) or cartilage-derived morphogenic protein-2 (CDMP-2) | BMP-13 |
|  | Growth/differentiation factor 5 (GDF-5) or cartilage-derived morphogenic protein-1 (CDMP-1) | BMP-14 |
|  | BMP-15 | BMP-15 |

Other families of growth factors have been shown to play a role in cartilage formation/differentiation. Among them the fibroblast growth factors (FGFs) are a family of polypeptide growth factors involved in a variety of activities. One of their receptors, FGF receptor 3 (FGFR-3) (Keegan K. et al., 1991 Proc. Nat. Acad. Sci. 88: 1095-99), is known to play a crucial role in chondrogenesis. Point mutations in the fgfr3 gene resulting in a ligand-independent constitutively active protein (which means that the FGF signalling is always active also in the absence of the ligand) cause skeletal abnormalities as achondroplasia and thanatophoric dysplasia.

As already outlined above, although autologous chondrocyte transplantation ("ACT") is becoming a widely accepted technique for repair of joint surface defects ("JSD") it still presents some drawbacks. More in detail, this procedure implies in vitro expansion—in the presence of autologous serum—of autologous chondrocytes obtained from an uninvolved area of the joint surface, followed by the implantation of the chondrocyte suspension under a periosteal flap sutured to seal the joint surface defect. Cell expansion is necessary to obtain from a small cartilage biopsy a number of cells sufficient to repair the cartilage defect. Expansion in monolayer result in the loss of phenotypic traits in chondrocytes (Benya and Shaffer. 1982, *Cell* 30:215-24). To date, however, it is not known how far it is possible to expand chondrocytes without hampering their phenotypic stability and therefore their capacity to form stable hyaline cartilage in vivo, resistant to vascular invasion and endochondral bone formation. Other factors that can affect the capacity of chondrocytes to form cartilage in vivo are the culture conditions, and several factors dependent on the donor such as age and pre-existing joint or systemic diseases. At the end of cell expansion the chondrocyte population is composed of some cells that retain their phenotypic stability, and others that still can proliferate but will not anymore contribute to cartilage repair. To obtain a consistent cell suspension for ACT, it is desirable to determine which is the actual capacity of the cells to form cartilage in vivo and, if necessary, to select stable chondrocytes within the expanded cell population. The importance of this issue is underscored by the large variability in the quality of the repair tissue obtained in a large series (Peterson et al. Clin Orthop [374], 212-234. 2000.) consisting of a range going from hyaline-like cartilage to fibrocartilage to no signs of repair.

Chondrocytes are the only normal skeletal cells known to grow anchorage-independent in agarose cultures (Benya and Shaffer. 1982, *Cell* 30:215-224). This culture system allows a recovery of some of the phenotypic traits that are lost with expansion in monolayer (Benya and Shaffer. 1982, *Cell* 30:215-224). The expression of type 2 collagen and the capacity to grow and rescue phenotypic traits in agarose culture, are good assays to evaluate chondrocyte differentiation and the potential to differentiate respectively. However they do not measure the capacity of chondrocytes to form cartilage in vivo.

SUMMARY OF THE INVENTION

The issues explained above clearly show that there is a long felt need for an assay to measure the capacity of expanded chondrocytes or other cartilage producing cells to form stable hyaline cartilage in vivo after in vitro expansion. Among skeletal cells the anchorage independent growth is specific for chondrocytes and chondrocytic precursors. Thus this property can be used as a quality control tool for chondrocyte-like cells. There is a need to identify molecular markers associated with specific cell types that would allow the clinician to produce suitable implants and to regenerate and repair cartilage tissue with the appropriate cells and avoid scar formation to the greatest possible extent. These goals and other purposes are achieved by means of the following objects of the present invention.

A first object of the present invention is to provide an in vivo assay to measure anchorage independent growth and phenotypic stability of a certain cell population, and more specifically to measure at the same time the anchorage-independent growth of cells and their potential to retain their commitment to a certain (original or induced by manipulation) differentiation pathway. A second object of the invention is the use of the aforesaid in vivo assay to evaluate the effect of a certain procedure or treatment administered to a certain cell population on its anchorage-independent growth as well as its phenotypic stability. A third object of the invention is the use of the aforesaid in vivo assay to predict the outcome of autologous chondrocyte transplantation ("ACT") using a certain population of expanded chondrocytes. A fourth object of the invention is the use of the aforesaid in vivo assay to identify molecular markers linked to the phenotypic stability of a certain cell population. A fifth object of the invention is the definition of a set of molecular markers linked to the outcome of the aforesaid in vivo assay using freshly isolated chondrocytes and therefore to the capacity to form stable cartilage in vivo. Another object of the invention is to provide a collection of candidate markers linked to the phenotypic stability of a certain cell population. Thus according to this embodiment markers are identified which are positively or negatively associated with chondrocyte phenotypic stability and can be used to assess the phenotypic stability of an isolated or expanded chondrocyte cell population. Alternatively they can be used to ascertain whether a cell population is capable of producing stable hyaline cartilage, independent of its origin or culture conditions. According to a particular embodiment of the present invention, one, more preferably two, especially preferably three to five, most preferably six or more markers obtained as described above are used for the identification and/or quality control of a phenotypically stable chondrocyte cell population or a population capable of producing stable hyaline cartilage for use e.g. in ACT. Yet another object of the invention is to provide an assay to assess the quality of a candidate marker for the determination of the phenotypic stability of a cell population.

Another object of the invention is the use of these positive and negative markers of chondrocyte stability as a tool to monitor, passage by passage, in vitro cell expansion and, more in general, the manufacturing process of chondrocyte expansion. This tool will be useful to optimise next generation chondrocyte expansion technologies and to predict when cell expansion must be stopped, to recover chondrocytes that have already lost their phenotypic stability only when needed, and especially to provide a quality control for chondrocytes to be used for ACT for lot release approval. This will make chondrocyte suspensions for ACT a more reliable and consistent product. A particular object of this invention is the use of defined positive and negative markers in FACS (Fluorescence Activated Cell Sorting) analysis and cell sorting in general to select, from a cartilage producing cell population, preferably from a chondrocyte population, only those cells that retain their phenotypic stability. Another object is to provide an implant comprising cells selected from a cell population as mentioned above. Another object of this invention is the use of cells selected from a cell population as mentioned above for a variety of clinical applications including transplantation into a patient through surgery or arthroscopic injection, namely to promote the repair or regeneration of damaged joints or joint surfaces, or seeding prosthetic devices. Yet another object of this invention is a therapeutic composition including cells selected by the above method for use in the said clinical applications.

Yet another object of the present invention is to provide a cell population or culture exhibiting chondrocyte phenotypic stability based on the detection of positive and/or negative markers associated with chondrocyte phenotypic stability. Most preferably said cells are characterized by the presence (or absence) of at least two, especially preferably at least six of said markers. According to a particular embodiment the cell population or culture is characterized by a particular ratio of cells showing positive and negative markers.

Yet another object of the invention is to provide a carrier such as a DNA chip with biomolecules capable of detecting the expression of the markers referred to above, such as oligonucleotides, to evaluate the phenotypic stability of cell populations, in a fast and practical way. For instance the oligonucleotides can represent one or more fragments of a cDNA sequence or a complementary sequence thereof or eventually the entire cDNA sequence of a marker or its complementary sequence.

DETAILED DESCRIPTION OF THE INVENTION

Figure 1:
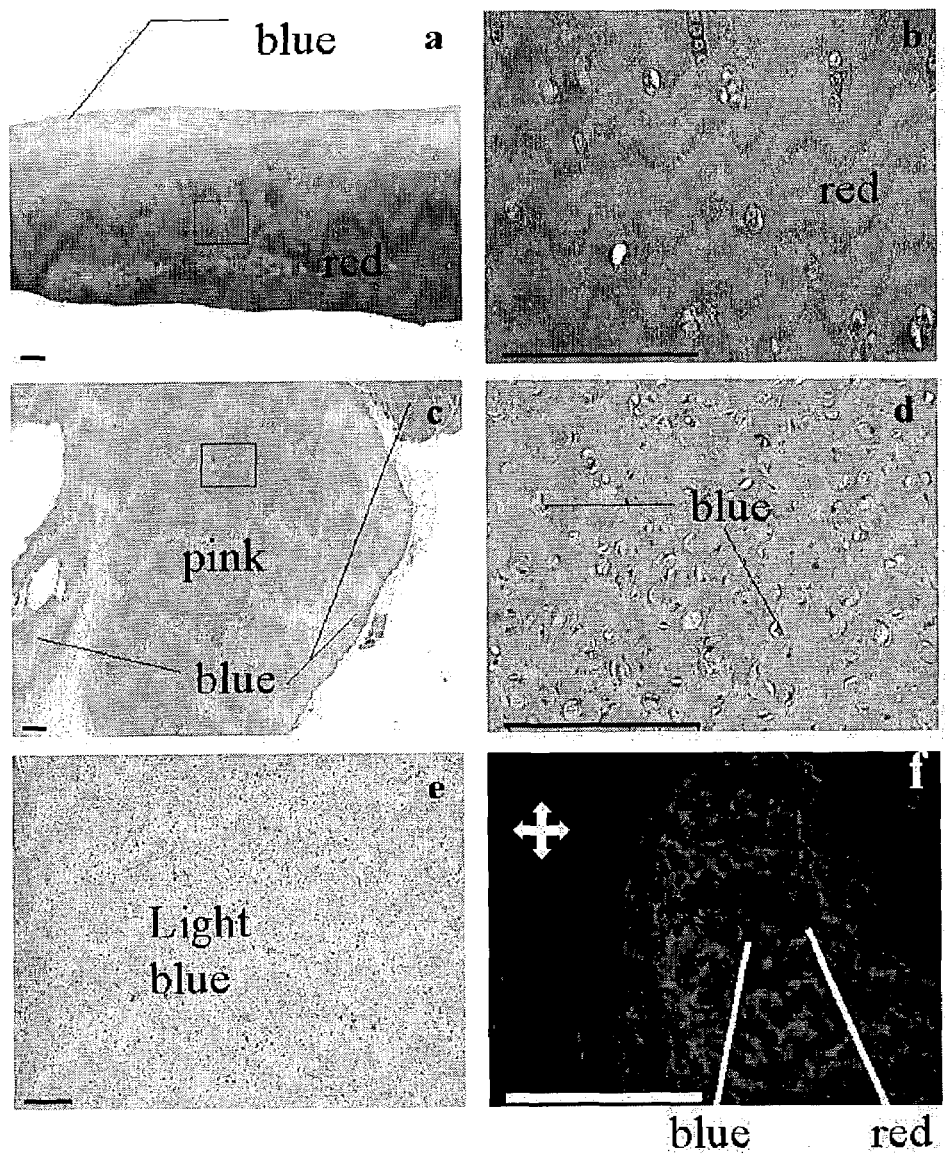
FIG. 1 is a set of 6 pictures showing the histological and histochemical characteristics and the expression of collagen type 2 of implants from the in vivo assay of the invention compared to human adult articular cartilage.

Abbreviations and accession number for markers mentioned throughout the disclosure:
Alk1: Activine A receptor Type II like kinase 1; Z22533
BMP2: Bone morphogenic marker; M22489
COL XI: Collagen type 11 alpha 1; J04177
FGFR3: Fibroblast growth factor receptor 3; M58051
Fritz: U91903
OPN: Osteopontin; X13694
PEDF: Pigment epithelium derived factor; M76979
RASF-PLA2: Phospholipase A2, Group IIA;J04704, M22430
Stromelysin: also known as MMP3 matrix metalloproteinase 3; X05232
Terms used throughout this disclosure are defined as follows:
Chondrocyte Stability
The capacity of a cell suspension, population or cell culture (either obtained from cartilage tissue or from any other tissue containing cells with chondrogenic potential) to produce upon injection in a mammal (in vivo), such as immune-deficient mice, (in a time frame of 3 weeks) a cartilage implant without signs of vascular invasion or endochondral bone formation.

Chondrogenic
The capacity to promote or stimulate cartilage growth. The term can apply to cells such as chondrocytes and to cells which themselves differentiate into chondrocytes. The term also applies to certain growth factors, such as TGF-$\beta$, which promote cartilage differentiation.

Co-expression and co-detectability
With co-expression or co-detection, in the context of the present invention, is meant that a second marker is expressed or detectable whenever a first marker is expressed or detectable. Thus, according to the present invention, particular markers such as BMP-2, FGFR-3 (positive markers) or ALK-1 (negative marker are found to be associated with chondrocyte phenotypic stability, based on the fact that they have a differential expression pattern in cell populations capable of producing stable hyaline cartilage in vivo and cell populations that do not produce such cartilage (as determined by the bio-assay described herein). The co-expressed or co-detectable markers referred to herein are those markers of which expression correlates with these markers in both cell populations. Preferably, according to the present invention, the markers co-expressed or co-detectable with the markers recited above, are selected from Stromelysin, RAS-PLA2, COL XI, Fritz, OPN (positive markers) or ALK-1 or PEDF (negative markers). Other markers co-expressed or co-detectable with the markers recited above are selected from those described in table 2A or 2B Such co-expressed or co-detectable marker can be a recognizable cell surface marker, detectable via polyclonal or monoclonal antibodies and/or specific ligands.

Connective Tissue
As used herein, any of a number of structural tissues in the body of a mammal including bone, cartilage, ligament, tendon, meniscus, dermis, hyperdermis, muscle, fatty, tissue, joint capsule.

Differentiation
A biological process by which primitive unspecialized cells acquire specialized function(s). Terminal differentiation provides a highly specialized cell having unique functional, genetic and phenotypic characteristics.

Marker
A marker as used herein refers to an expressed DNA sequence, for Which expression is associated with a trait, characteristic or function. The markers of the present invention are sequences for which expression is associated with the ability to produce stable hyaline cartilage in vivo (e.g. as measured in the bioassay described herein). Thus, there is a difference in expression of these markers between cell populations that are capable of producing articular cartilage and populations that are not. Preferably this positive or negative correlation is maintained upon subsequent passaging of the cells. According to the present invention, markers are preferentially detected at the RNA level, using methods known in the art (as described in the examples). However, it can be envisaged that other detection methods, e.g. at the protein level are used. According to a preferred embodiment said marker is selected from a comparative micro-array of the two described populations, based on the sort score value, which is representative for the differential expression. However, it is understood that markers selected in such a way should preferably be confirmed, either by repeated micro-arrays or by individual determination of expression in the respective cell populations.

Marker Protein

A polypeptide that distinguishes one cell (or set of cells or cell population or culture) from another cell (or set of cells or cell population or culture) and is associated to a peculiar biological function. For example, the surface antigen CD3 is expressed or is detectable on the surface of T lymphocytes but not on other types of lymphocytes (e.g. B, or null lymphocytes) and serves as a marker protein for this subset of lymphocytes. When the marker protein is a cell-suA dispersion of lipid particles according to claim 1, wherein the said dispersion is combined with a biologically active molecule, wherein the said biologically active molecule is a macromolecule selected from the group consisting of nucleic acids, DNA, RNA, mRNA, rRNA, tRNA, uRNA, ribozymes, antisense oligonucleotides, peptide nucleic acid (PNA), plasmid DNA, polypeptides, glycosylated polypeptides, proteins, glycosylated proteins, protamine salts and sugars.

rface antigen, like for instance hormone receptor, antibodies that bind the marker protein can be used in cell sorting methods, e.g., to produce a population of cells enriched for cells that express the marker protein. Alternatively, intracellular proteins can be used as marker proteins. For example, fluorescent or luminescent proteins, such as green fluorescent protein (GFP) and aequorin (GFP of *Aequoria victoria*) (Tanahashi et al (1990), *Gene* 96: 249-255) can be used as the marker protein and can facilitate cell sorting, e.g., by FACS. Also enzymes can be used, provided that the activity of the enzyme can be detected. For example, β-galactosidase is well suited for use as a marker protein; this enzyme can be detected by introducing into the cell a substrate(s) that release a fluorescent product(s) upon cleavage by the enzyme (available from, e.g., Molecular Probes). Another suitable enzyme is catechol 2,3-dioxygenase, which is encoded by xy/E of *Pseudomonas putida* (Domen et al (1986), *Anal Biochem* 155: 379-384).

Operably Linked

Connection of a coding sequence and (a) regulatory sequence(s) (e.g., a promoter) in such a way as to permit gene expression when the appropriate molecules (e.g., transcriptional activator proteins) are bound to the regulatory sequence(s).

Osteogenic

The capacity to promote or to generate the production of bone. The term may be applied to osteoblasts which have the capacity to promote bone growth, or to cells which themselves are able to differentiate into osteoblasts. The term would also apply to growth factors having the ability to promote bone growth.

Phenotypic Stability

Maintenance of the ability of any cell to organize or reorganize, in vivo, the structure of a specific tissue, either the original tissue where the cells were taken from, or a different tissue the cells have been forced to form under specific conditions.

Promoter

A nucleotide sequence sufficient to direct transcription of a coding sequence. Included within the invention are those promoters which are inducible by external signals or agents; such elements can be located in the 5' or 3' untranslated regions (UTR) of the native gene. A "FGFR-3 promoter" is any sequence contained within the UTR of the endogenous FGFR-3 gene that is sufficient to direct transcription of FGFR-3 in FGFR-3 positive cells like stable chondrocytes. For example, a 3-Kb sequence immediately adjacent to the FGFR-3 transcription start site is sufficient to direct FGFR-3 gene expression. It is recognized that in genetic constructs containing a FGFR-3 promoter (e.g., those constructs that also contain a reporter gene or a gene encoding a marker protein), minor variations (e.g., deletions, point mutations, and the like) can be made in the sequence of the FGFR-3 promoter without abrogating its ability to be active in phenotypically stable chondrocytes and not in other chondrocytes. Thus, FGFR-3 promoters having such minor variations without abrogating the specificity of the promoter are encompassed by the term "FGFR-3 promoter". In addition, multiple copies of the FGFR-3 promoter, arranged in tandem, can be used to direct gene expression.

Reporter Gene

Any gene for which expression can be monitored. Commonly used reporter genes include, for example, genes encoding chloramphenicol acetyltransferase, alkaline phosphatase, luciferase, and green fluorescent protein.

Stable Cartilage

Cartilage not finally turning into bone, i.e. cartilage devoid of any signs of vascularization. Particularly, the stable cartilage in accordance with the present invention is human adult or mature articular cartilage but may also include animal adult or mature cartilage. Contrary to stable cartilage, transient cartilage in the end will become bone tissue. In the context of the present invention, cartilage is said to be stable if, even after e.g. seven weeks, any signs of bone formation are absent.

Stem Cell

Pluripotent precursor cell having the ability to self-renew and to generate a variety of differentiated cell types. True stem cells can divide indefinitely. With embryogenic stem cells are understood the pluripotent cells of normal karyotype derived from a blastocyst.

Detailed Description of the Embodiments and Examples

The present invention is based on the possibility to measure and verifiably ascertain the capacity of isolated connective tissue cells to produce the relevant tissue in vivo using a nude mouse model. First, this capacity is linked to a set of molecular markers. Secondly, the presence of the molecular markers is associated with the outcome of connective tissue defects such as joint surface defects ("JSD") repair in well-standardized animal models of JSD. Thirdly, membrane-associated molecular markers can be used to select, from an expanded connective tissue cell population, only those cells that, retaining their phenotypic stability, will be able to optimally repair JSD. The set of molecular markers (both membrane-associated and/or non membrane-associated) can also be used to identify cells or cell populations capable of producing stable hyaline cartilage or as a final quality control for the cell suspension to be used for implantation such as ACT or the repair of a tissue, thus providing a reliable and consistent final product.

A first embodiment of the present invention consists of an in vivo assay which measures the capacity of isolated cells to reproduce in vivo a certain tissue with all its cellular and extra-cellular components, i.e. all its specific characteristics. This assay-devised to measure chondrocyte stability but extendible to any cell population involved in a certain differentiation pathway—consists of an in vivo assay to measure anchorage-independent growth and phenotypic stability of a certain cell population, comprising subcutaneous or intramuscular injection in a mammal animal, preferably in an immune-deficient animal, of a cell suspension in an iso-osmotic liquid. After a certain period of time (corresponding to the time needed to obtain measurable tissue formation) the animal is sacrificed and the implant is evaluated. For chondrocytes, the same suspension comprises articular chondrocytes in an amount equivalent to about $1\times10^6$ (preferably from $2\times10^6$ to $20\times10^6$) chondrocytes as applied to immune-deficient mice. In the case that the mammal is a mouse, the in vivo assay consists of the injection of a single cell suspension, for example intramuscularly, in immune-deficient nude mice. After a certain period of time, at least 3 weeks, the mouse is sacrificed, dissected, and the implant, if retrieved, weighed, fixed and histologically evaluated. The in vivo assay of the invention as performed for cartilage is highly specific since about $5\times10^6$ freshly isolated articular chondrocytes injected in a volume of 50-100 µl of any iso-osmotic liquid such as phosphate buffered saline (PBS) or HBSS, are sufficient to yield after 3 weeks an implant of mature cartilage. The same number of expanded periosteal cells yield a fibrous tissue histologically resembling periosteal tissue. Young periosteal derived cells (PDCs), i.e. PDCs from individuals younger than 20 and preferably younger than 16, cultured and expanded under appropriate conditions, however, yielded stable cartilage implants. On the contrary, the injection of cell lines known to have in vitro osteo-chondrogenic potential—namely ATDC5, CFK2, RCJ, and C5.18 cells—did not yield any retrievable implant. Importantly, serially passaged (P4 and P5) articular chondrocytes, still retaining their anchorage-independent growth and rescuing the expression of type 2 collagen in agarose culture (according to the method of Benya et al. (1982) Cell (1):215-24) failed to yield an implant. This finding is of particular importance because it demonstrates that the agarose assay—thus far considered a stringent assay for the phenotypic stability of expanded chondrocytes (Brittberg et al. N Engl J Med. 1994 Oct. 6; 331(14):889-95)—is not sufficient to predict the capacity to form cartilage in vivo. From this it is clear that the well-known agarose assay is unable to function as a quality control method for determining when cartilage is in a suitable state to be implanted. Strikingly, epiphyseal chondrocytes (which in normal embryonic development undergo endochondral ossification and are destined to be substituted by bone) yield a cartilaginous implant in which vascular invasion, chondrocyte hypertrophy and bone formation are taking place.

A second embodiment of the invention is the use of certain specific conditions of the in vivo assay of the first embodiment to evaluate the possibility that a certain procedure or treatment administered to a certain cell population involved in a certain differentiation pathway can hamper its anchorage-independent growth as well as its phenotypic stability. For instance, while enzymatic release of the cells by enzymatic treatment induces no such risk, on the contrary extensive cell expansion (after 2-3 passages) compromises the ability of connective tissue cells such as chondrocytes to yield a cartilaginous implant in the in vivo assay. On the other hand, the in vivo assay also evaluates whether a certain treatment, such as addition of growth factors/reagents, or procedure, such as physical stimulation, enhances the phenotypic stability of cell populations. For instance, treating the cell suspension for 30 minutes with CDMP-1 (100 ng/ml; stock solution in 45% acetonitrile, 0.1% trifluoroacetic acid) just before injection, followed by washing two times in PBS, resulted in a three fold increase in the wet weight of the retrieved implant as compared to control injections, and in a 2 fold increase in the number of cells. Such enhancement can allow a dramatic reduction of the expansion needed for tissue repair (in some cases and ultimately making in vitro expansion not needed at all) and consequently a corresponding reduction of the risk to make connective tissue cells phenotypically unstable.

A third embodiment of the invention is the use of the in vivo assay of the first embodiment to predict the outcome of autologous cell transplantation ("ACT") using a certain population of cells involved in a certain differentiation pathway (e.g. expanded chondrocytes) as a means to predict phenotypic stability (e.g. chondrocyte stability). This can be evaluated either using well-standardized animal models for ACT or using an ex vivo system. This ex vivo system consists of placing articular cartilage, with or without underlying bone, in culture (liquid, solid or semi-solid), producing a cartilage defect, with or without a natural or synthetic membrane to cover the lesion, and applying, underneath the membrane, a cell population either in suspension, or seeded within a carrier, with or without growth factors to mimic in vitro the events that take place in vivo during JSD repair.

A fourth embodiment of the invention is the use of the in vivo assay of the first embodiment to identify molecular markers linked to the phenotypic stability of a certain connective tissue cell population involved in a certain differentiation pathway, e.g. chondrocytes. These molecular markers can be identified by comparing the gene expression between cells that are capable and cells not capable of producing stable hyaline cartilage (as measured in the in vivo assay). For example, markers can be identified by semi-quantitative RT-PCR, by Northern hybridization (as explained in example 4 below), by the generation of subtracted libraries from cell population that succeed in the in vivo assay matched to similar cell populations that fail (e.g. serially passaged chondrocytes), by differential display or subtractive hybridization approaches, or by DNA arrays or DNA chips. Such DNA chips can hold all known genes involved and/or just not involved with chondrocyte stability. EST (expressed sequence tags) can be used to identify and provide information on previously unknown genes. A set of such genes can be identified by comparing the outcome of cell populations that form good connective tissue and preferably stable connective tissue with the outcome of cell populations that fail to do so. A third population used in the comparative test may comprise a connective tissue cell population (e.g. chondrocytes) that forms connective tissue (cartilage in the case of chondrocytes) in vitro as long as a trigger is present (e.g., TGF-β1), but that loses this capacity once the trigger is removed from the culture medium and that fails to form a retrievable cartilage implant in vivo. A set of positive and negative markers for connective tissue cell (e.g. chondrocytes) phenotypic stability, consisting of at least 2, preferably at least 6 to monitor connective tissue cell quality and at least 6, but most preferably at least 20 markers is used to monitor efficiently and unequivocally said connective tissue cell quality, independent of its origin. Preferably, the outcome is linked to ratios of markers or thresholds therefor (taking into account differences in expression and possible gradual up-regulation or down-regulation of markers). Preferably the predictive value of the set of markers is further increased by analyzing the effect of independent variables (age, gender, background, co-morbidities) on the final outcome of the ACT procedure. This can be done by storing in a database all the data of the individual patient together with the expression of the molecular markers and a score that describes the outcome of the procedure (based on pain, function of the joint, stiffness of the repair tissue by indentometry, and eventually histological and molecular analysis of biopsy of the repair tissue). The influence of the independent variables on the predictive value of our set of markers will be determined by statistical analysis of the data.

DNA chips (or genosensors) are miniature arrays of surface-tethered (c)DNA probes (typically oligonucleotides but also longer DNA probes) to which a nucleic acid sample (the "target" sequence) is hybridized. In the context of the present invention, DNA chips can be used as diagnostic tools to rapidly conclude on chondrocyte phenotypic stability. A marker can be represented by one large oligonucleotide covering the entire cDNA sequence of its gene, but also by one or more oligonucleotides from different regions of the cDNA sequence. The sequences can have the sense as well as the antisense direction of the DNA. The aim is to produce digital hybridization fingerprints that can be interpreted by computer and for which ratios of "positive" and "negative" markers can be generated. Genosensors can harbor hundreds to thousands (e.g., 12.000) of DNA probes, useful for high throughput DNA marker analysis and messenger RNA profiling (differential display on a chip). Alternatively, smaller sets of probes, duplicated in subarrays across the chip, can be used to interrogate numerous samples in parallel. Oligonucleotides are either synthesized in situ on the support surface of the DNA chip (in situ attachment strategy), or, alternatively, pre-synthesized oligonucleotides are attached to each site in the array (post-synthesis attachment strategy). The phosphoramidite method of solid phase chemical synthesis is used to generate the oligonucleotides in both cases (Matteuci and Caruthers (1981), *J Am Chem Soc* 103: 3185-91). The post-synthesis attachment strategy is easy to implement using commercially available equipment and materials (Beattie, In Caetano-Anolles, Gresshoff (ed), *DNA Markers. Protocols, applications and overviews*. Wiley-VCH, New York, p213-224). More advanced options are available for preparation of higher density arrays (Microfab technologies Inc.: Eggers et al, (1994), *BioTechniques* 17: 516-525; Accelerator Technology Corp.: McIntyre (1996), *IBC Conference on Biochip Array Technologies*, Marina del Rey, Calif.; Mirzabekov group: Yershov et al (1996), *Proc Natl Acad Sci USA* 93: 4913-4918; Khrapko et al (1991), *FEBS lett* 256: 118-122; Mirzabekov (1994), *Trends Biotechnol* 12: 27-32). Support surfaces comprise glass, such as microscopy slides, and microchannel glass (Tonucci et al (1992), *Science* 258: 783-785) or porous silicon (Lehmann (1993), *J Electrochem Soc* 140: 2836-2843) for use in a flowthrough genosensor (Beatti et al, (1995), *Clin Chem* 41: 700-706). In the latter, hybridization occurs within three-dimensional volumes, providing an approximately 100-fold greater surface area per unit cross section compared with two-dimensional flat surface designs, greatly increasing thereby the binding capacity per hybridization cell and providing an improved detection sensitivity etc. (Doktycz and Beattie (1996), in: Beugelsdiik A (ed), *Automated Technologies for Genome Characterization*. John Wiley & Sons, New York; Beattie (1996), In: Sayler GS(ed), *Biotechnology in the Sustainable Environment*. Plenum Publishing Corp, New York; Beattie et al (1996), In: Schlegel J (ed), *Pharmacogenetics: Bridging the Gap between Basic Science and Clinical Application*. IBC Biomedical Library, Southborough, Mass. Oligonucleotide probes are covalently linked to, e.g., silicon dioxide surfaces by applying the methods of Lamture et al (1994), *Nucleic Acid Res* 22: 2121-2125; Beattie et al (1995), *Clin Chem* 41: 700-706, *Mol Biotechnol* 4: 213-225; Doktycz and Beattie (1996), In: Beugelsdiik A (ed), *Automated Technologies for Genome Characterization*. John Wiley & Sons, New York; Beattie (1996), In: Sayler GS(ed), *Biotechnology in the Sustainable Environment*. Plenum Publishing Corp, New York; or Beattie et al (1996), In: Schlegel J (ed), *Pharmacogenetics: Bridging the Gap between Basic Science and Clinical Application*. IBC Biomedical Library, Southborough, Mass. Protocols for attachment to glass surfaces, using 3'-propanolamine oligonucleotides (Genosys Biotechnologies, The Woodlands, Tex.) and to microscopy slides are available from Beattie (Caetano-Anolles, Gresshoff (ed), *DNA Markers. Protocols, applications and overviews*. Wiley-VCH, New York, p213-224) and Beattie et al (1995), *Mol Biotechnol* 4: 213-225. A robotic fluid dispensing system is commercially available (e.g. Hamilton Microlab 2200 system equipped with 21G needles and 50 µl syringes), capable of robotically dispensing droplets as small as 10 nL onto glass slides at 1mm center-to-center spacing (Beattie et al (1995), *Clin Chem* 41: 700-706, *Mol Biotechnol* 4: 213-225).

Genosensors and diagnostics in accordance with the present invention may be used to diagnose the state of cells and cell cultures but may also be used in situ to determine the vitality of human or animal connective tissue such as cartilage.

A fifth embodiment of the invention is the identification of a set of molecular markers linked to the outcome of the in vivo assay of the first embodiment, using freshly isolated or serially passaged cells from a certain cell population involved in a certain differentiation pathway, e.g. chondrocytes, and therefore linked to the phenotype (e.g. chondrocyte) stability. For instance, freshly isolated human chondrocytes were used for RNA purification and cultivated in vitro. Upon passaging, an aliquot of cells was used for RNA purification, 2 aliquots of $5 \times 10^6$ cells were injected in the in vivo assay and the rest re-plated. RNAs were tested by semi-quantitative RT-PCR for expression of genes known to have a role in chondrogenesis and cartilage maintenance.

In the PCR analysis were also included genes isolated from a subtracted cDNA population obtained by a subtractive hybridization approach: cDNA from pig P0 chondrocytes (stable in the in vivo assay) was matched against cDNA from P1 chondrocytes (that failed to yield an implant) in a two-way subtractive hybridization. Individual cDNAs from both subtracted cDNA populations (P0-P1 and P1-P0) were cloned in PCR-Script Amp SK(+) vector, and sequenced. The human homologues, when known, were included in the RT-PCR analysis. Unknown cDNAs were evaluated for differential expression by Northern analysis.

Micro arrays can be used to provide a pool of candidate markers. In a first step the mRNA of two populations of cells (a population of cells identified as stable in the in vivo assay and one that failed to yield an implant) are differentially labelled and hybridized with an array of probes covering a large number of genes. The results of this micro array analysis provide a number of candidate markers, i.e. genes that have a high probability to be differentially expressed in one population compared with the second population. The Sort Score in the micro-array provides a measure of the differential expression of the genes in the two populations. Preferably, the positive candidate markers are markers with a Sort Score below −1,0 and the negative candidate markers are markers with a Sort Score above +1,0. According to the present invention, at least 142 positive markers with a sort score of less than 1, and 113 negative markers with a sort score greater than 1 can be identified (Table 2A and 2B). It is understood however, that other factors, such as intensity of expression or the encoded protein, can also influence selection of the candidate marker.

Optionally, the candidate markers can be confirmed in a second step. In this second step primers are designed to assay an individual candidate marker by RT-PCR in different independently obtained samples from both populations of cells. This RT-PCR analysis firstly provides an alternative method to assay a candidate marker identified by the micro array analysis, and secondly provides an assay wherein the quality of a candidate marker is tested on multiple independent results, as is shown in the examples.

Results from first experiments had indicated that strong expression of markers such as BMP-2, FGFR-3, are positively associated to chondrocyte stability, whereas activin-like kinase (ALK)-1 expression is negatively associated. The absence of a negative marker can be interpreted as a positive marker. Micro-array results have further provided a large number of co-detectable positive and negative markers of which RASF-PLA2, stromelysin type, Fritz, type XI collagen and type II collagen have been validated to be positively associated to chondrocyte stability and PEDF has been validated to be negatively associated to chondrocyte stability.

Other markers co-expressed or co-detectable with respectively FGFR-3 or BMP-2 and ALK-1 and that therefore predict their expression, can be used for quality control and fall within the scope of the present invention. The molecular marker expression can be detected at the mRNA level (e.g., via RT-PCR), at the protein level (e.g. via specific antibodies-polyclonal or monoclonal—via specific ligands (e.g., FGF9 is a specific ligand of FGFR-3). Fluorochrome-labelled FGF-9 could be used to select FGFR-3 expressing cells via FACS, or FGF-9 coated magnetic beads could be used to sort FGFR-3 expressing cells via a magnetic field (Dynabeads).

Alternatively, the detection of the molecular markers such as FGFR-3 can be indirect via specific target genes or any other component of the FGFR-3 pathway, via reporter constructs (indirect method based on detection of FGFR-3 promoter activity or promoters that are specifically activated upon FGFR-3 signaling controlling the expression of a heterologous reporter gene). Polyclonal or monoclonal antibodies are preferentially raised against the extracellular domain of the receptor so that the antibodies can be used for cell sorting like FACS (see above). More specifically, that is hydrophilic and therefore readily accessible and that is specific to FGFR-3. Mouse, rabbit, or any other suitable species IgM/IgG antibodies of the present invention are raised against a fragment of FGFR-3, e.g. against the region between the I and the II immunoglobulin-like loop of the extracellular domain of the FGFR-3. A peptide suitable for raising suitable antibodies has the amino acid sequence TGLVPSERVLVG-PQRLQVLNASHEDSGAYSCRQRLTQRVL [SEQ ID NO:1]. The full nucleotide sequence of the FGFR-3 receptor is publicly available (Genbank accession number M58051) Antibodies raised against other such domains of the FGFR-3 receptor fall within the scope of the present invention.

Other validated candidate markers which are selected from the microarray analysis and which are membrane bound proteins with an extracellular domain can be used for raising antibodies and could thus be detected at the protein level. Methods for raising such antibodies are well known in the art and are for instance described In Ausubel et al (ed.), *Short Protocols in Molecular Biology*, $4^{th}$ edition, John Wiley & Sons, New York, and more specifically units 11.3, 11.4 and 11.5; In Paul (ed.), Fundamental immunology, $4^{th}$ edition, Lippincott-Raven Publishers, New York, and more specifically chapter4, p 101 ef; de St. Groth and Scheidegger (1980), *J immunol Methods* 35:1-21; French et al (1986), *Immunol Today* 7:344-346; Langone and Vunakis (1986), *Methods in Enzymology*, vol 121, *Immunochemical Techniques. Part I, Hybridoma technology and monoclonal antibodies*. Orlando: Academic Press; Hämmerling et al (1981), *Monoclonal antibodies and T-cell hybridomas. Perspectives and technical advances*. Amsterdam: Elsevier/North-Holland Biomedical Press; Yokoyama (1995) In Coligan et al (ed), *Current protocols in immunology*, Wiley & Sons, New York, 2.5.1-2.2.17; Kohler and Milstein (1975), *Nature* 256: 495-497. Also possible is the derivation of monoclonal antibodies from e.g. phage display libraries (Paul (ed), Fundamental immunology, $4^{th}$ edition, Lippincott-Raven Publishers, New York, and more specifically chapter4, p 101 ef; de Bruin et al (1999), *Nature Biotechnology* 17(4): 397-399).

A sixth embodiment of the invention is the use of the positive and/or negative markers associated with chondrocyte phenotypic stability to identify cells or cell populations capable of producing stable hyaline cartilage in vivo, e.g. cells to be used for autologous cell transplantation. Preferably, the markers are used to identify stable chondrocytes within a chondrocyte cell population. According to one aspect of the invention at least two, preferably three to five, most preferably at least six markers are used to positively identify a population capable of producing stable hyaline cartilage in vivo. Alternatively, the markers are used to identify stable cartilage producing cells within an undefined cell population. Preferably, at least two, more preferably at least six, most preferably at least ten markers are used to positively identify a population capable of producing stable hyaline cartilage in vivo, independent of its origin. It is understood that if candidate markers are used, a larger number of markers will provide a more reliable identification. Moreover, preferably identification of the cell population is based on the ratio of positive marker for chondrocyte phenotypic stability over negative marker for chondrocyte phenotypic stability being greater than 1, preferably greater than 2.

Thus, according to this embodiment the positive and/or negative markers of connective tissue phenotype (e.g. chondrocyte) stability can be used either individually or in combination, as tools to monitor passage by passage cell expansion, namely to predict when cell expansion must be stopped and/or to recover connective tissue cells (e.g. chondrocytes) that have already lost their phenotypic stability only when needed, and eventually to provide a means for quality control of connective tissue cells (e.g. chondrocytes) to be used for autologous cell transplantation ("ACT"), thus making connective tissue cell (e.g. chondrocyte) suspensions for ACT a more reliable and consistent product.

A seventh embodiment of this invention is the use of FACS analysis and other cell sorting methods to select, from a connective tissue cell (e.g. chondrocyte) population, only those cells that retain their phenotypic stability. "Positive" membrane-associated markers (e.g. FGFR-3 or markers co-detectable with FGFR-3, FGFR-3 reporter activity, or components of the FGFR-3 signaling pathway that report FGFR-3 activation) will be used for positive selection of cells with phenotypic stability (e.g. stable chondrocytes), while "negative" membrane-associated markers (e.g. ALK-1 or markers co-detectable with ALK-1) will be used to sort out cells without phenotypic stability (e.g. unstable chondrocytes). The positive and negative markers may be used individually or combined. The consistency of the selection will be monitored by the detection of unrelated, non membrane-associated markers such as BMP-2 and type II collagen in the sorted population, thus significantly enriching the cell population to be used for ACT with cells with connective tissue phenotypic stability (e.g. stable chondrocytes) and consequently increasing quality and efficiency of the whole procedure. FACS is one of the conventional cell sorting methods used to sort a specific cell population out of a heterogeneous cell suspension. Antibodies raised against specific cell markers are labelled to fluorochromes and are mused to label the cell population that expresses that marker. The fluorescence is used to sort individual cells by mean of a specific technology (Beckton Dickinson). Methods to fluorescently label antibodies are known in the art and many such antibodies are commercially available. Alternatively, an unlabeled antibody can be use to specifically bind the cell surface polypeptide, and a second, labelled antibody can then be used to specifically bind the first antibody. Other techniques, such as the use of protein-conjugated magnetic beads that selectively bind particular cells, can also be used. Suitable kits are commercially available. Generally, such kits utilize a tagged antibody (e.g., a biotin-labelled antibody) to bind the cell surface marker protein. The antibody-bound cells are contacted with a magnetic bead-protein conjugate, where the protein portion of the bead-protein conjugate specifically binds the tagged antibody. For example, a streptavidin-magnetic bead conjugate can be used to bind the biotin-tagged antibody to produce a complex containing the magnetic bead-protein conjugate, the tagged antibody, and the cell expressing the marker protein. Such complexes can be separated from other cells by temporarily adhering the complex to a magnet and separating the adhered cells from the other cells (i.e., a population of cells depleted for connective tissue cells, e.g., phenotypically unstable chondrocytes). Magnetic beads that are covalently coupled to a secondary antibody are commercially available. Other antibody-based methods for sorting cells, like the use of affinity chromatography or the retaining of cells expressing the particular cell surface proteins via Petri dishes coated with antibodies directed against the latter, also are known in the art and can be used in the invention. A useful, commercially available affinity cell separation kit, "CEPRATE LC", may be obtained from CellPro (CellPro, Inc. Bothell, Wash. 98021).

Methods of connective tissue cell sorting may involve selecting cells based on suitable ratios, e.g. the ratio of cells expressing a positive marker mentioned above to a negative marker mentioned above. Preferably, the ratio is such that the cells with positive markers are in the majority, that is the ratio of cells with positive to cells with negative markers is 1 or greater than 1, preferably 2 or greater than 2.

Another embodiment of this invention comprises cells and in using cells retaining connective tissue phenotypic stability and selected from a cell population by means of the above selection method for a variety of clinical applications. The cells are typically human adult or mature connective tissue cells exhibiting phenotypic stability. The cells are particularly human adult or mature articular cartilage cells but may also include animal adult or mature cells exhibiting the same properties. These cells may, for instance, be transplanted without further processing to a connective tissue site in a patient to promote the repair or regeneration of damaged bone or cartilage. Unlike previous methods, the present invention does not necessarily require (as explained in the second embodiment) in vitro culturing in order to obtain a suitable (both in nature and quantity) cell population for use for in vivo application. By way of example, the said selected cells retaining phenotypic stability may be implanted at any connective tissue site needing cartilage regeneration by any implanting procedure such as surgery or arthroscopic injection. Another clinical application of such cells involves seeding any prosthetic device intended to be anchored into a mammal host in order to improve the attachment of the said device This includes knee and hip replacement devices made from organic or inorganic materials having low immunogenic activity such as titanium alloys, ceramic hydroxyapatite, stainless steel and cobalt-chrome alloys. Another example is the use of said cell population to create and improve sphincter function by means of the formation and maintenance of a cartilaginous support, for instance around the urethra for stress incontinence.

In yet another embodiment the ratio Cell$^+$/Cell$^-$ of cells expressing BMP-2 and/or FGFR-3, stromelysin, RASF-PLA2, Col XI, Fritz, OPN and/or markers co-detectable with these markers and/or specific reporter constructs or molecules belonging to the specific intracellular signaling pathways as molecular markers positively associated with chondrocyte phenotypic stability to cells expressing activin-like kinase-1 (ALK-1), PEDF and/or markers co-detectable with this marker and/or specific reporter constructs or molecules belonging to the specific intracellular signaling pathways as molecular markers negatively associated with chondrocyte phenotypic stability is greater than 1, preferably greater than 2. The cells or cell culture may be in a form suitable for implantation in a human or animal.

Yet another embodiment of this invention consists of a therapeutic composition including cells or cell populations selected or identified by the above methods for use in the said clinical applications. The cells are mature or adult cells which exhibit phenotypic stability. In addition to the selected cells, the composition usually includes at least a pharmaceutically acceptable carrier, well known to those skilled in the art and for instance selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregeletanized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like. When the therapeutical composition is intended for transplantation to a site in the body needing repair, it may additionally include at least one growth factor of the TGF-β, family.

A more complete understanding of the present invention will be obtained by referring to the following illustrative examples.

EXAMPLE 1—CARTILAGE OBTAINMENT AND CELL ISOLATION

Articular cartilage was obtained, within 24 hours after death unless otherwise indicated from human donors not having suffered from any articular disease. After macroscopic inspection to rule out gross joint pathologies, cartilage was sliced full thickness from femoral condyles and placed in Hank's Balanced Salt Solution ("HBSS") (available from Life Technologies) supplemented with 200 units/ml penicillin, 200 μg/ml of streptomycin, and 0.5 μg/ml of amphotericin B (Life Technologies). After two washes in HBSS during 5 minutes at 37° C., cartilage was finely minced and placed in a sterile 0.2% crude collagenase (Life Technologies) solution in Dulbecco's Modified Eagle Medium ("DMEM") with high glucose (Life Technologies) containing 10% foetal bovine serum ("FBS") (Biowittaker), 200 units/ml penicillin, 200 μg/ml of streptomycin, and 0.5 μg/ml of amphotericin B. After overnight incubation at 37° C., cells were washed twice in culture medium—DMEM supplemented with 10% FBS, 100 units/ml penicillin, 100 μg/ml of streptomycin, and 0.25 μg/ml of amphotericin B—and counted with trypan-blue exclusion test to adjust for the number of viable cells.

EXAMPLE 2—IN VIVO ASSAY

Cells isolated in example 1 were washed twice in sterile phosphate buffered saline ("PBS"), re-suspended in a volume of 100 μl of PBS and injected intramuscularly in the thigh of female, 4-5 weeks old immune-deficient nude mice. Animals were sacrificed after 3 weeks by cervical dislocation and the thigh dissected to retrieve the presence of the implant in the site of injection. Implants were weighed, and either snapfrozen and stored in liquid nitrogen for in situ hybridization or fixed in freshly-made 4% formaldehyde for 4 hours for histology and immunohistochemistry. After fixation the samples were included in paraffin, cut in 5 µm thick sections and colored according to standard protocols (Alcian blue pH 2.5, Toluidine blue, Masson's trichrome, Safranin O) (Manual of Histological Techniques). Different amounts of cells, from $20 \times 10^6$ to $5 \times 10^5$ were used for injection in order to establish the minimum amount of cells that yielded a cartilage implant. Although the minimal amount of freshly isolated chondrocytes that yielded an implant was $1 \times 10^6$, as an optimal amount we chose to use $5 \times 10^6$ cells because this number always yielded at least one implant in duplicate injections when freshly isolated chondrocytes where used.

FIG. 1 shows that freshly isolated or early passage adult human articular chondrocytes generate cartilage tissue after intramuscular injection in nude mice. (a) and (b) Safranin O stainings of adult human articular cartilage harvested from the femoral condyle. (c) and (d) Safranin O staining of a cartilage implant. (b) and (d) are details from (a) and (c) as indicated by the boxes in (a) and (b), respectively. Compared to adult human articular cartilage, the implant is hypercellular. Masson's trichrome staining in (e) displays the absence of neoangiogenesis or endochondral bone formation. (f) Immunofluorescence for collagen type 2 is brightly positive in the ECM of the implant. Dark spots are blue. Lighter colour is red. Adjacent muscle tissue is indicated with an asterisk. Nuclei are counterstained with DAPI. The scale bar is 200 µm.

In order to check that viable cells were needed to organize the cartilage implant, an equal number of cells that had been killed by freezing and thawing three times in liquid nitrogen were injected. Those injections yielded no implant. We also investigated whether cells should be able to proliferate, we irradiated freshly isolated chondrocytes with a single dose of 50 Gy, a dose that blocks proliferation but is not lethal to the cells. Except for some cytological atypies, the injections yielded an otherwise normal hyaline cartilage implant.

Strikingly, the injection of embryonic epiphyseal chondrocytes (which in normal embryonic development are replaced by bone) yield implant with vascular invasion and endochondral bone formation. These data demonstrate the fine specificity of the in vivo assay in reporting the phenotypic pathway the injected cell is placed in.

Figure 2:
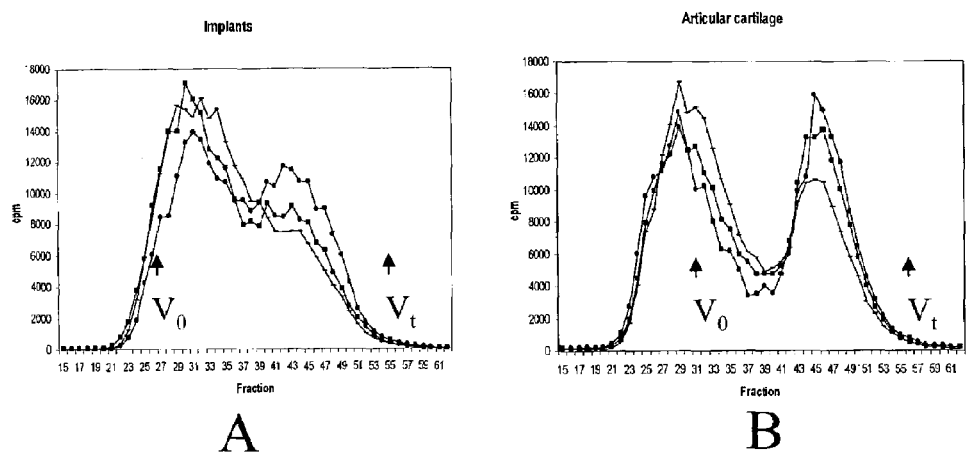
FIG. 2 are two charts (A, B) showing the hydrodynamic profile of sulphated proteoglycans in implants (A) from the in vivo assay of the present invention and in human adult articular cartilage (B).

To investigate the hydrodynamic profile of sulphated proteoglycans (an important component of the extracellular matrix of cartilage) we performed [35S]SO4 incorporation and size fractionation of macromolecules in both the implants and the native human articular cartilage. FIG. 2 shows the presence in 3 implants (A) of high molecular weight proteoglycans with the same hydrodynamic size as in adult human articular cartilage explants (B). The high molecular weight proteoglycans (left peak) are present in both implants and articular cartilage. This molecular weight fraction is specific for cartilage tissue.

Figure 3:
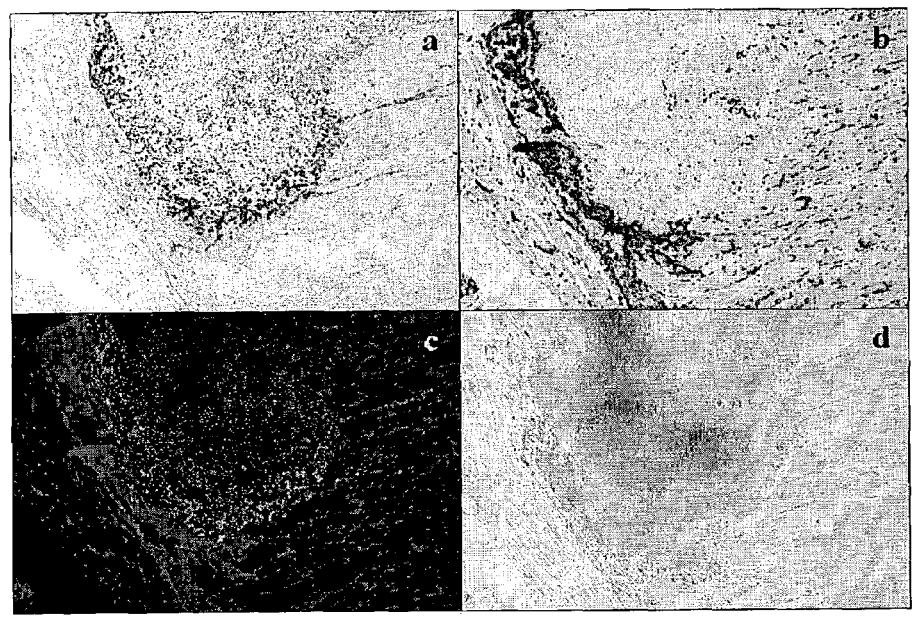
FIG. 3 is a set of four pictures showing in situ hybridization for human-specific Alu repeats (A), mouse specific L1 repeats (B), a supposition of A and B (C) and toluidine blue staining (D) of an implant from the in vivo assay of the invention.

In order to investigate whether the cartilage implant is made of cells of human origin, i.e. to rule out that the only role of the injected cells is producing factors that induce chondrogenesis in the mouse muscle), we performed in situ hybridization for human specific Alu repeats as described by Kuznetsov et al.(1997), *J Bone Miner.Res.*(9):1335-47 and mouse-specific L1 repeats. This procedure demonstrated that cells contributing to cartilage formation in our in vivo assay are of human origin, i.e. derive from the injected cells and not from the mouse host. FIG. 3 shows the origin of the implant. Consecutive sections where hybridized with human (a) or mouse (b) specific probes recognizing genomic repeats (Alu and m-L1 respectively). (c) is a superimposition of (a) and (b) using artificial colors. The intermingling of human and mouse cells at the left edge of the implant was due to infiltration of chondrocytes in between the muscle fibers as showed in the toluidine blue staining in (d). The scale bar is 200 µm.

EXAMPLE 3

Serial Passaging Results in Impaired Chondrocyte Stability.

Cartilage samples from 3 independent human donors were placed in monolayer culture. Upon passaging, an aliquot of cells was destined to duplicate injection in the in vivo assay of example 2 and to RNA isolation. Chondrocyte stability, as measured by the retrieval of a cartilage implant after 3 weeks in the site of injection, was lost between passage 1 and 3.

EXAMPLE 4

Molecular Markers Associated with Chondrocytic Stability

Three pools of human articular chondrocytes were obtained as described in example 1 and cultured in monolayer. Upon passaging, 2 aliquots ($5 \times 10^6$ cells each) were injected in the in vivo assay of example 2, a smaller aliquot was used to obtain the RNA extract and the rest was re-plated. Total RNAs were reverse-transcribed using Thermoscript (available from Life Technologies) and used for semi-quantitative PCR analysis. After passage 5, two samples were placed in low melting-agarose cultures, a system known to result in a rescue of type II collagen expression by de-differentiated chondrocytes. After 2 months, colony formation was abundant and cultures were harvested for RNA extraction. Semi-quantitative RT-PCR analysis was carried out for expression of genes involved in chondrogenesis.

In order to explore the role of genes unknown to be involved in chondrogenesis, we also undertook a differential expression analysis based on the principle of subtractive hybridization: pig articular chondrocytes were plated and cultured in monolayer. Upon passaging cells were assayed for chondrocyte stability and RNA was isolated. Poly $A^+$ RNA was purified using Oligotex mRNA Mini Kit (available from Quiagen) from total RNA derived from P0 and P1 cells. We chose those two populations because P0 cells still yielded a cartilage implant in the in vivo assay of example 2 while P1 cells did not. cDNAs were reciprocally subtracted in order to obtain species differentially expressed by P0 cells (potential positive markers of stable chondrocytes) and species differentially expressed by P1 cells (negative markers). Subtraction and amplification of subtracted cDNAs were performed using PCR-Select™ cDNA subtraction Kit (available from Clontech). cDNAs were cloned in PCR Script amp SK (+) vector and sequenced. Genes of which human homologue was known were included in the semi-quantitative RT-PCR analysis on human samples, while unknown genes were controlled for their differential expression in the original RNA population by Northern analysis. The detailed procedures used were as follows:

RNA Preparation

Total RNA from chondrocytes was isolated using Trizol reagent (available from Life Technologies), ethanol precipitated and stored at −70° C. for further use. Total RNA from agarose cultures was obtained by homogenizing the whole culture in 6M urea, 3M lithium chloride with a Polytron homogenizer, and the major part of agarose was removed by centrifugation at room temperature at 3000 rpm for 15 minutes. Nucleic acids in the supernatant were allowed to precipitate overnight at 4° C., pelleted by centrifugation 15 minutes at 18000 rpm at 4° C., supernatant was removed, RNA was air dried and dissolved in RNAse-free water. Residues of agarose and other contaminants were removed by phenol-chlorophorm extraction followed by ethanol precipitation. Samples were re-dissolved in RNAse-free water and stored at −70° C. for further use. For those samples requiring mRNA selection, poly A+ tailed RNA was sorted out of total RNA by double selection using Oligotex mRNA Mini Kit (Quiagen).

Semi-quantitative RT-PCR Analysis

1 μg of total RNA was first strand-transcribed using Thermoscript (Life technologies). Before PCR analysis, cDNAs were equalized for β actin. PCR for human β actin was carried out in a volume of 10 μl stopping the reaction after 18, 19, 20 cycles to make sure that PCR amplification was still in an exponential phase. PCR products were electrophoresed in 1% agarose gel in TBE buffer, stained with ethidium bromide and the intensity of the bands was analyzed by densitometry using Image Master software (available from Pharmacia-Biotech). cDNAs were diluted according to the relative intensity of the bands. To rule out that β actin was differentially regulated in the different samples to be compared, the same analysis was also performed for GAPDH mRNA. After equalization for β actin, all samples were simultaneously tested for a number of genes known to be involved in chondrogenesis and cartilage maintenance. The same analysis was performed for those molecules obtained with a subtractive hybridization approach. For each gene, cycling was optimized in such a way that amplification was still in an exponential phase when PCR was stopped for all samples.

Figure 4:
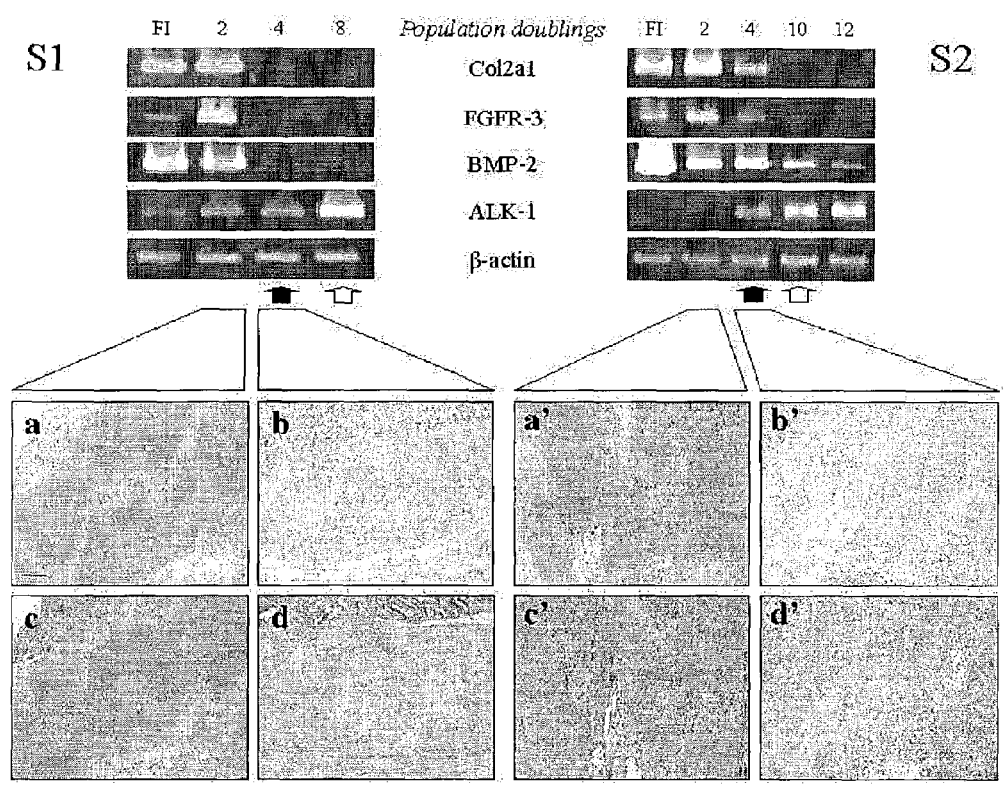
FIG. 4 is a set of pictures showing the molecular profile (by RT-PCR) of articular chondrocytes during in vitro expansion and the respective histology after 2 and 4 population duplications.

FIG. 4 shows that serial expansion of human adult articular chondrocytes results in the loss of their capacity to form cartilage in vivo. Samples from 2 independent donors (S1 and S2) were expanded. Upon passaging, aliquots of the cell suspension were injected in nude mice or used for gene expression analysis. After 2 population duplications, chondrocytes could still form mature cartilage tissue as evaluated by alcian blue (a and a') and safranin O (c and c'). After 4 population doublings—black arrow—the loss of cartilage forming ability was heralded by the formation of more immature implants as shown by alcian blue (b and b') and safranin O (d and d') stainings. Chondrocytes from further passages—open arrow—did not form any retrievable implant. The loss of the cartilage forming potential was marked by downregulation of type 2 collagen, Fgfr3, and Bmp2 mRNA, while the expression of Alk1 mRNA was upregulated. FI is freshly isolated chondrocytes. Scale bar is 200 μm. The appearance of the negative marker ALK-1 is associated with or heralds the state of non-formation of a retrievable implant and the appearance of this negative marker is associated with downregulation of the positive markers.

Figure 5:
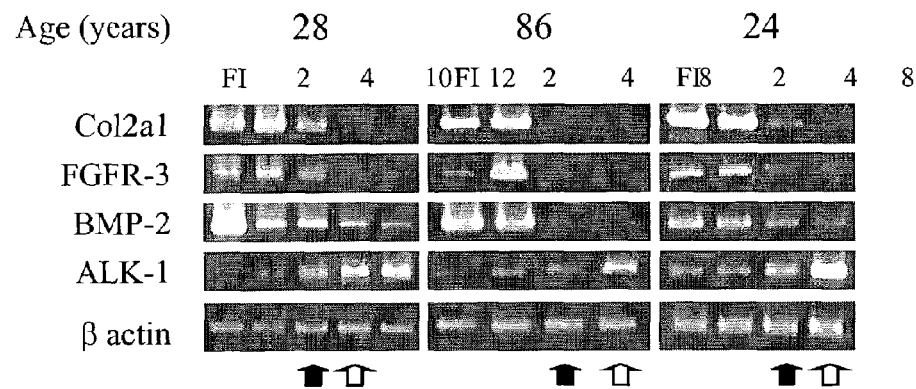
FIG. 5 is a set of pictures showing the molecular profile of articular chondrocytes from donors of different ages during in vitro expansion.

FIG. 5 shows that the set of molecular markers predict the capacity of AHAC to form stable cartilage in vivo independently on the donor age. Freshly isolated (FI) and serially passaged chondrocytes from donors of different ages (range 28-86 yr old) were challenged in our in vivo assay throughout expansion. The black arrow marks the passage when a decline of the maturity of the implant was first detected. The open arrow marks the first passage from which no implant could be retrieved. Again the downregulation of the positive markers is followed by upregulation of the negative marker ALK-1 and, at the same time, the appearance of ALK-1 heralds the stage at which no implant can be retrieved.

Figure 6:
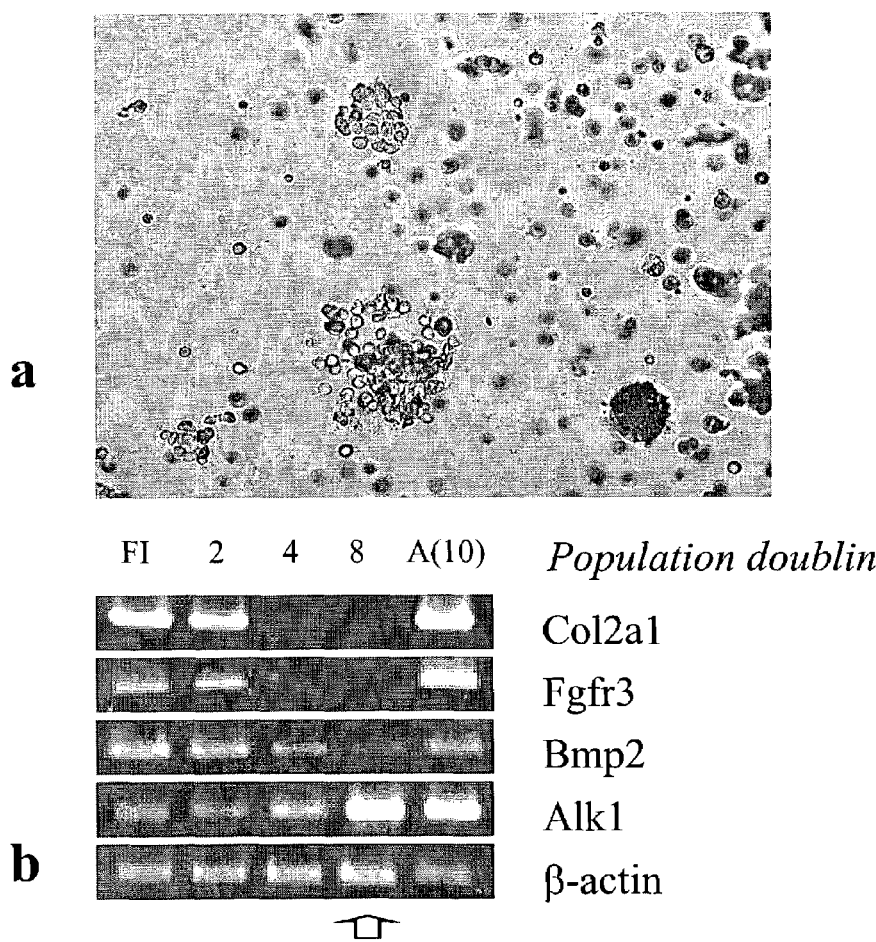
FIG. 6 is a set of pictures (B) showing the results of RT-PCR analysis for various molecular markers in articular chondrocytes throughout passaging and in passaged chondrocytes that had been challenged with the agarose assay. The figure also shows a picture of chondrocytes cultured in low melting agarose (A).

FIG. 6 shows that the agarose assay does not predict the cartilage tissue forming ability of expanded chondrocytes in our in vivo assay. Freshly isolated (FI) and serially passaged adult human articular chondrocytes were injected in nude mice and tested in the agarose assay. (a) Although the cells lost their in vivo cartilage tissue forming ability after the second passage, they could still grow in anchorage independent conditions in agarose after passage 5 (about 10 population duplications). (b) The molecular profile of the same chondrocytes throughout passaging and after agarose culture is shown at A(10). FI stands for freshly isolated chondrocytes. The arrow indicates the first passage from which no implant could be retrieved. Although there has been rescue of the positive markers the negative marker was still upregulated and these cells did not form cartilage in vivo. This is a clear demonstration that positive marker presence, e.g. FGFR3, is indicative of healthy cartilage but is not necessarily exclusively indicative thereof. Hence, the use of negative markers alone to sort or to use a combination of positive and negative markers are preferred embodiments of the present invention.

EXAMPLE 5

Figure 7:
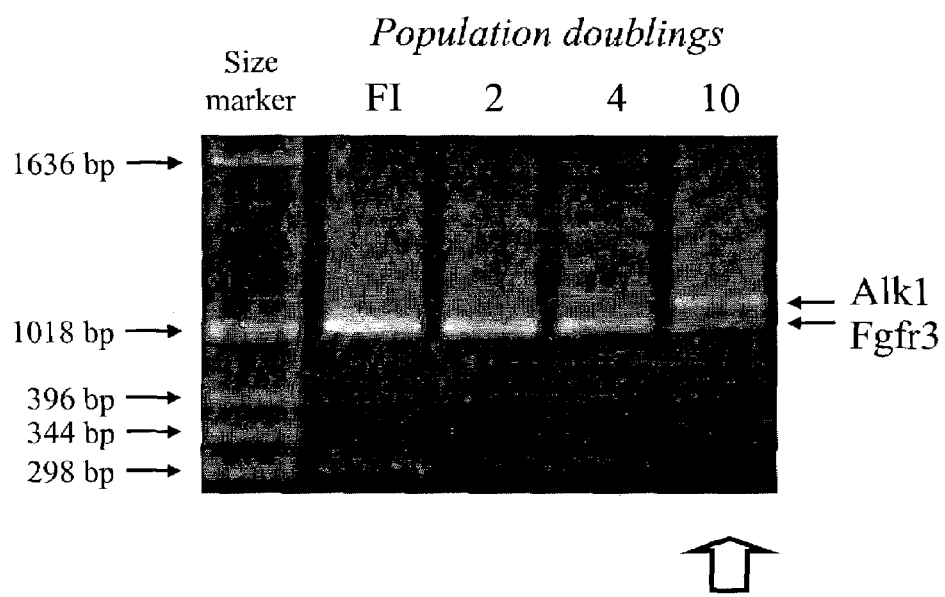
FIG. 7 is a picture showing RT-PCR analysis for Fgfr3 and Alk1 performed in the same tube of chondrocytes throughout in vitro passaging.

FIG. 7 shows that the presence of a negative marker for chondrocyte stability offers the possibility of an internal control for expression levels. RT-PCR for FGFR3 and Alk1 in the same tube is performed from freshly isolated (FI) and expanded chondrocytes at different passages. The appearance of the higher band corresponding to Alk1 and the decrease of the Fgfr3 band marks the loss of the capability to organize a cartilage implant in vivo. The arrow indicates the first passage from which no implant could be retrieved. This is coincident with the appearance of the negative marker ALK-1 and disappearance of the positive marker FGFR3.

EXAMPLE 6—THE IN VIVO ASSAY AND THE SET OF MARKERS FOR PREDICTING THE OUTCOME OF AUTOLOGOUS CHONDROCYTE TRANSPLANTATION (ACT) IN AN ANIMAL MODEL

Male young New Zealand white rabbits or goats are used as a model of ACT. Articular cartilage of the patella or femoral condyles are carved with a device producing a superficial cartilage defect 0.3 mm deep and 3 mm large in diameter, therefore not penetrating the underlying bone. Human articular chondrocytes are expanded to various extents as disclosed in example 1, analyzed for the presence of markers associated with chondrocytic stability according to example 4 and injected back in the cartilage lesion under the periosteal flap as described by Brittberg et al. (1996) Clin.Orthop.(326):270-83. After three months the animals are sacrificed and the joint surface defect analyzed and scored by histology for the extent and quality of cartilage repair and for integration of the margins. In situ hybridization for human Alu repeats is carried out in order to investigate the contribution of injected chondrocytes to the cartilage repair.

In a different approach we have devised an ex vivo model of JSD repair by ACT. The whole patella was excised from a male young New Zealand white rabbit, a cartilage defect was generated and previously isolated chondrocytes were injected underneath a periosteal flap sutured to cover the lesion. The patella was then placed in culture in DMEM supplemented with 10% FBS and antibiotic-antimycotic solution at 37° C. in 5% $CO_2$ atmosphere. After 2 weeks the patella was fixed in 4% formaldehyde, imbedded in paraffin and analyzed for histology and other techniques.

This setting allows tighter and more controlled experimental conditions and also a closer and much more flexible monitoring of the healing process by means of e.g. cell labelling, time point biopsy of the healing tissue for histological and molecular analysis etc.

EXAMPLE 7—RESCUE OF SERIALLY PASSAGED ARTICULAR CHONDROCYTES

A short treatment with a growth factor from the TGF-β superfamily just before implantation can partially rescue serially passaged articular chondrocytes that have just lost phenotypic stability or reduce dramatically the cell expansion procedure occurring before cells can be injected for joint surface defects repair, ideally eliminating the need of it. The treatment is administered to cells in suspension for a short time and is followed by extensive washes in PBS just before injection. Similarly treated cells are tested for the expression of molecular markers linked to phenotypic stability of the articular chondrocyte.

Figure 8:
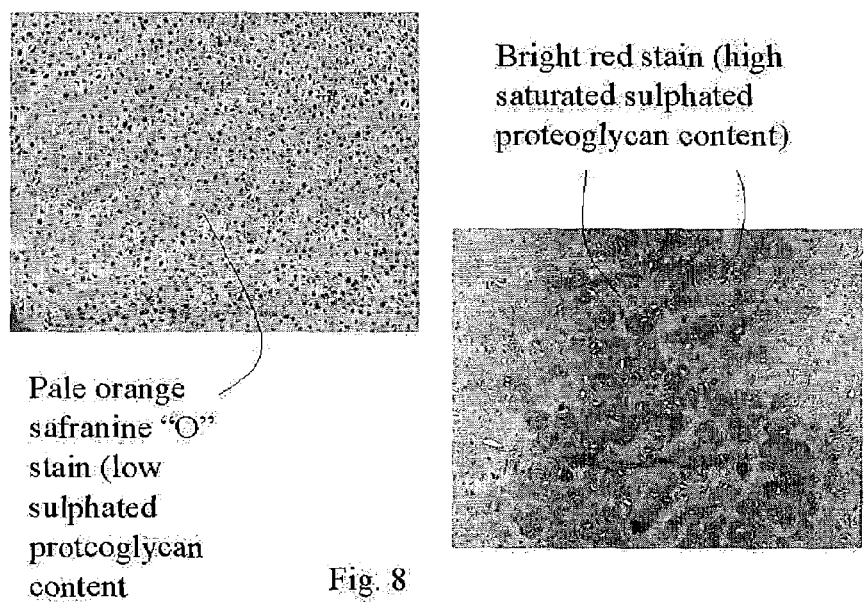
FIG. 8 is a set of two pictures showing implants obtained by injecting chondrocytes previously treated with or without CDMP1.

In a set of experiments, freshly isolated articular chondrocytes in single cell suspension were exposed for 30 minutes to 100 ng/ml of CDMP-1 in Nutrient Mixture Ham's F-12 (Life Technologies) at 37° C., washed twice in PBS and injected in the in vivo assay of example 2. Control injections were made with chondrocytes exposed to HAM-F12 alone. After 3 weeks cartilage implants were weighed, digested in 0.2% crude collagenase at 37° C. and isolated cells were counted. The implant obtained from CDMP-1 treated cells had a wet weight three times higher as compared to samples treated with HAM-F12 alone, and cell count was twice as high. As shown in FIG. 8, also the production of highly sulphated proteoglycans was enhanced as witnessed by a more intense metachromatic staining with Safranin O in the implant obtained from CDMP-1 treated chondrocytes (FIG. 8B) as compared to control (FIG. 8A). This shows that a short exposure to CDMP-1 in suspension, just before injection, is capable of enhancing the chondrocytic phenotype as measured by the in vivo assay of example 2. Furthermore, the effectiveness of such short pulse makes prolonged, expensive and potentially dangerous expansions unnecessary.

EXAMPLE 8—ISOLATION OF STABLE CHONDROCYTES FROM A MIXED CELL POPULATION BY THE USE OF FLOW-CYTOMETRY

During cell expansion, as demonstrated in example 4, some chondrocytes become phenotypically unstable and unable to organize cartilage tissue in vivo. As a consequence, the chondrogenic potential of an expanded chondrocyte population depends not only from the mere number of cells but also from the number of phenotypically stable chondrocytes that it contains. The identification of membrane-associated molecular markers for both stable and unstable chondrocytes—for instance FGFR-3 and ALK-1 respectively or any markers co-detectable therewith—gives the opportunity to select optimal cells for ACT. The entire expanded cell population is incubated with antibodies directed to ALK-1 and/or FGFR-3, or any membrane-markers co-detectable therewith, labelled with different fluorochromes. FACS analysis on double-labelled or multi-labelled cells depicts the distribution of stable and unstable chondrocytes within the total pool. If needed, cell sorting is used to separate the stable from the unstable chondrocytes (e.g. using positive markers) or to sort the unstable from the stable (e.g. using negative markers). A small aliquot of the sorted stable chondrocyte population is used for quality control using, for example, other independent positive and negative markers of chondrocyte stability (e.g. type II collagen and BMP-2 as positive markers and ALK-1 as negative marker). The remaining stable chondrocytes are recovered in culture medium containing autologous serum and prepared for ACT. This allows obtaining a cell suspension composed of a consistent number of stable chondrocytes, suitable for implantation or for use in a pharmaceutical composition, all or a majority of the cells contributing to cartilage repair and not being a mixture of heterogeneous cells regardless of their phenotype. It also allows eliminating from the pool unstable chondrocytes that not only are unable to generate cartilage in vivo but can potentially hamper the appropriate repair.

EXAMPLE 9—EXPRESSION PATTERN OF TYPE 2 COLLAGEN AND FGFR3

Figure 9:
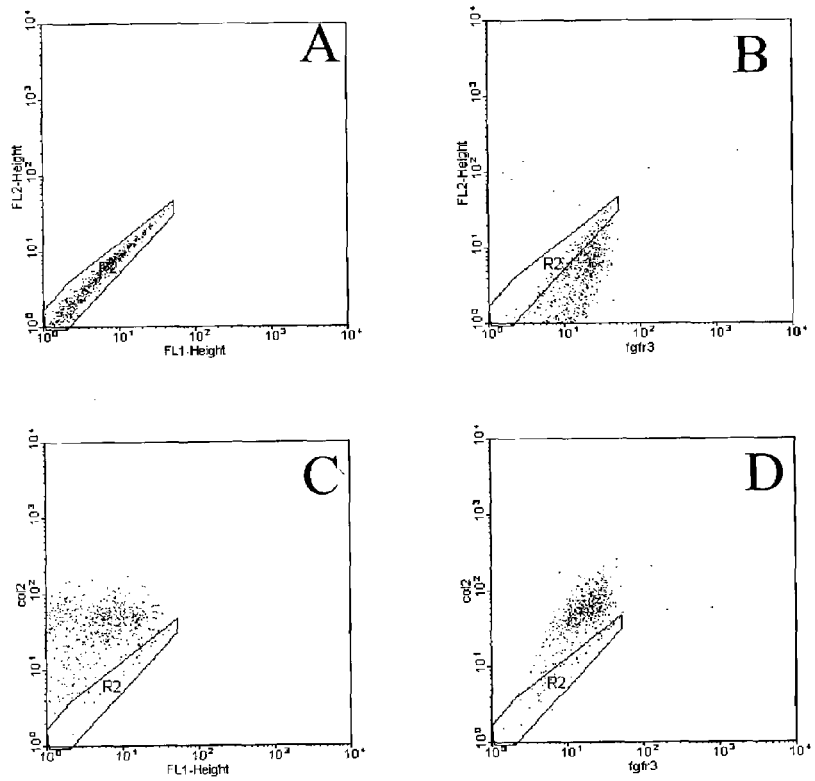
FIG. 9 is s set of four graphs obtained by flow-cytometric analysis, (a) unlabeled, (b) labelled with rabbit human FGFR3 antibody, (c) labelled with mouse anti-human collagen type 2 antibody and (d) with both antibodies.

FIG. 9 shows that most cells isolated from human adult articular cartilage co-express type 2 collagen and FGFR3 simultaneously. Cells were released from cartilage tissue by enzymatic digestion in 0.2% collagenase overnight, permeabilized using Fix&Pem reagent (Sigma) and either left unlabeled (A) or labeled with rabbit anti-human FGFR3 antibody (B), or labeled with mouse anti-human collagen type 2 antibody (C) or labeled with both of these (D). Fluorescein or phycoerytrin conjugated antibodies to, respectively, rabbit or mouse IgG were used as secondary antibodies. Flow-cytometric analysis shows that 80% of the cells are positive for FGFR3 (in B) and 85% of the cells for collagen type 2 (in C). Panel D shows that individual cells are co-expressing both FGFR3 and collagen type 2 indicating that FGFR3 is present in fully differentiated cells and is not a marker for skeletal precursor cells.

EXAMPLE 10—Prediction of the Quality of Implants

The present invention also includes cells and cell cultures which express positive and negative markers described above in specific ratios. Due to commercial, practical and time restraints it is not always possible to carry out the cell sorting methods described above such that every cell expresses positive markers and does not express negative markers.

In order to determine the ratio of cells with positive markers (Cell$^+$) to those with negative markers (Cell$^-$) the in vivo assay and diagnostic methods described above have been used on human cell populations to determine when a satisfactory implant can be expected, i.e. that the implant will produce healthy stable cartilage. These experiments show that when the ratio Cell$^+$/Cell$^-$ is 1 or above suitable implants may be prepared from such a cell population. Preferably, the ratio is 2 or more. A ratio of 5 or more is considered to provide a significant security of a successful implant. The ratio may be advantageously obtained from examination of the DNA chips described above.

EXAMPLE 11—IDENTIFICATION OF CANDIDATE MARKERS

Microarray

To expand the number of molecular markers associated to the capacity of expanded chondrocytes to form cartilage tissue in vivo, differential gene expression analysis was performed using microarray technology (Affymetrix) comparing RNA from primary confluent (P0) adult human articular chondrocytes—capable to form cartilage in a well-validated nude mouse model (Dell'Accio,F., De Bari,C., and Luyten,F. P. (2001). In Arthritis Rheum. 44, 1608-1619.)—to RNA from chondrocytes at the third passage (P3) that had failed to form cartilage in vivo in the same model. Gene expression by freshly isolated (FI) chondrocytes—positive in the mouse assay—was included in the comparison to exclude genes that are only linked to in vitro culture and not necessarily linked to phenotypic stability. As an additional control, RNA was added from early passage periosteal cells (hpp3) that generated stable cartilage in the mouse assay—and from the same periosteal cells at passage P10 (hpp10), when they had lost this property. This latter RNA pair was added to identify markers that are associated to stable-cartilage forming cells, independently of their origin.

Total RNA was purified using Trizol reagent (Life Technologies), precipitated and resuspended in water. RNA quality was assessed by agarose gel electrophoresis in denaturing conditions.

The microarray analysis was performed using an Affymetrix micro array covering 12,000 human genes according to the manufacturer's protocols.

The results of the microarray have been analyzed and are summarized in table 2.

We considered as positive markers those with a sort score below a certain value, e.g. <−1,0 and as negative markers those with a sort score above a certain value, e.g. >1,0. Some of the positive markers were present in the periosteal cells at an early passage, e.g. passage 3, and absent in the periosteal cells at a later passage such as passage 10. These markers were considered to be putative predictive markers of the capacity to form cartilage in vivo regardless of the cell origin (mature cells from the articular cartilage or precursors from the periosteum).

Table 2: Result of Micro Array Analysis p Explanation of the column headers (bold items appear as column headers in the analysis output):

Descriptions: Gene accession number in Genbank and brief description of Diff Call (Difference Call): There are 5 possible outcomes for difference call. The level of expression of an RNA is increased (I), decreased (D), marginally increased (MI), marginally decreased (MD) or there is no detectable change in expression level (NC).

Fold Change: The fold change is the ratio of the average differences (Avg Diff) between the experimental and baselines files (average difference between expression at P3 and expression at P0). This number reflects the magnitude of the change, but not the direction of the change (refer to Diff Call).

Sort Score: Sort Score is based on both Fold Change and Avg Diff change. This score can be used to evaluate the differences in the expression of genes between the experimental and baseline files (difference in expression between P0 and P3).

$$\text{SortScore} = \text{sign}(FC)\sqrt{|\Delta I|} * \log|FC| * 10^{(x-1-1/3)}$$

$$x = \frac{|\max(Q_m * Q, I_{exp}) - \max(Q_m * Q, I_{bl})|}{\max(Q_m * Q, I_{exp}) - \max(Q_m * Q, I_{bl}) + 1}$$

$$\Delta I = I_{exp} - I_{bl}$$

Sign (FC) is the sign (+ or −) of the fold change.

I=Average Difference

Absolute Call (Abs Call): There are 3 possible outcomes in Abs Call: "P" (present), "A" (absent), and "M" (marginal).

Log Average Ratio (Log Avg): log average ratios for different experimental conditions, is a measure for intensity.

TABLE 2A

RESULT OF MICRO ARRAY ANALYSIS: POSITIVE MARKERS
Positive markers: entries are ranked on sort score, the description column contains the Genbank Accession number and a short description of the protein encoded by it. The other column headers are explained above.

| Descriptions | Diff Call | P3-P0 Fold Change | P3-P0 Sort Score | Absolute call | | | | | log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| Cluster Incl. X68733:*H. sapiens* gene for alpha1-antichymotrypsin, exon 1/ | D | −104.1 | −46.46 | P | P | M | P | A | 4.96 | 3.51 | 0.92 | 4.94 | 0.22 |
| Cluster Incl. L10347:Human pro-alpha1 type II collagen (COL2A1) gene exons 1-54 | D | ~−153.4 | −45.02 | P | P | A | P | A | 6.06 | 6.9 | −0.06 | 6.64 | −0.79 |
| Cluster Incl. M22430:Human RASF-A PLA2 mRNA, complete cds | D | −76.6 | −34.8 | P | P | P | P | A | 5.97 | 5.64 | 1.48 | 3.37 | −0.27 |
| M22430/FEATURE=/DEFINITION= HUMRASFAB Human RASF-A PLA2 mRNA, complete cds | D | −44.6 | −28.42 | P | P | P | P | A | 4.85 | 4.04 | 1.32 | 5.13 | 0.9 |
| Cluster Incl. L41162:*Homo sapiens* collagen alpha 3 type IX (COL9A3) mRNA, complete cds | D | ~−82.9 | −28.19 | P | P | A | P | A | 8.53 | 7.81 | −0.63 | 7.82 | −0.1 |
| X05232/FEATURE=cds Human mRNA for stromelysin | MD | −24.3 | −22.34 | P | P | P | P | A | 4.94 | 4.14 | 3.84 | 8.03 | 0.67 |
| Cluster Incl. AL049250:*Homo sapiens* mRNA; cDNA DKFZp564D113 (from clone DKFZp564D113) | D | −47.1 | −21.65 | P | P | M | P | A | 6.24 | 3.34 | 1.07 | 2.62 | 1.21 |
| Cluster Incl. AF052124:*Homo sapiens* clone 23810 osteopontin mRNA, complete cds | D | ~−54.2 | −19.87 | P | P | A | A | A | 7.2 | 2.13 | 0.42 | 1.93 | 1.52 |
| Cluster Incl. U91903:Human Fritz mRNA, complete cds | D | ~−48.4 | −18.1 | P | P | A | P | A | 7.9 | 7.27 | 0.91 | 5.84 | −1.01 |
| Cluster Incl. X01683:Human mRNA for alpha 1-antitrypsin | D | −14.8 | −16.88 | P | P | P | P | M | 6.51 | 4.15 | 2.66 | 5.8 | 1.29 |
| Cluster Incl. M68516:Human protein C inhibitor gene, complete cds | D | ~−42.7 | −16.16 | P | P | A | A | A | 6.24 | 2.69 | −1.35 | −0.92 | −0.96 |

TABLE 2A-continued

RESULT OF MICRO ARRAY ANALYSIS: POSITIVE MARKERS
Positive markers: entries are ranked on sort score, the description column contains the Genbank Accession number and a short description of the protein encoded by it. The other column headers are explained above.

| Descriptions | Diff Call | P3-P0 Fold Change | P3-P0 Sort Score | Absolute call | | | | | log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| Cluster Incl. X58079:Human mRNA for S100 alpha protein | D | −28.7 | −15.32 | P | P | P | P | A | 6.2 | 5.1 | 1.99 | 4.87 | 0.84 |
| M22489/FEATURE=/DEFINITION=HUMBMP2A Human bone morphogenetic protein 2A (BMP-2A) mRNA | D | −33.9 | −14.94 | P | P | A | P | A | 7.13 | 6 | 0.52 | 4.32 | 1.42 |
| Cluster Incl. AL031228:dJ1033B10.12 (collagen, type XI, alpha 2 (COL11A2)) | D | −36 | −14.34 | P | P | A | P | A | 5.14 | 4.77 | 1.05 | 4.36 | −0.34 |
| Cluster Incl. M55153:Human transglutaminase (TGase) mRNA, complete cds | D | ~−37.0 | −14.25 | P | P | P | P | P | 5.9 | 6.77 | 1.89 | 5.95 | 5.25 |
| Cluster Incl. L20971:Human phosphodiesterase mRNA, complete cds | D | −21.7 | −13.51 | P | P | A | P | P | 8.55 | 8.92 | 1.37 | 7.87 | 3.1 |
| Cluster Incl. U24578:Human RP1 and complement C4B precursor (C4B) genes, partial cds | D | ~−38.0 | −13 | P | P | A | A | A | 3.14 | 1.72 | 0.92 | 0.57 | 0.68 |
| Cluster Incl. M22489:Human bone morphogenetic protein 2A (BMP-2A) mRNA | D | −22 | −11.38 | P | P | A | P | A | 6.21 | 5.51 | 1.46 | 4.29 | 1.56 |
| J04765/FEATURE=/DEFINITION=HUMOSTRO Human osteopontin mRNA, complete cds | D | ~−28.7 | −11.21 | P | P | A | P | A | 7.79 | 1.97 | 0.11 | 2.28 | −0.84 |
| U04636/FEATURE=mRNA/DEFINITION= HSU04636 Human cyclooxygenase-2 (hCox-2) gene, complete cds | D | −24.3 | −10.93 | P | P | M | P | P | 5.74 | 7.78 | 1.24 | 7.28 | 3.08 |
| Cluster Incl. M13699:Human ceruloplasmin (ferroxidase) mRNA, complete cds | D | −8.5 | −9.35 | P | P | P | P | M | 7.68 | 4.61 | 3.62 | 4.55 | 1.05 |
| Cluster Incl. AJ224741:Homo sapiens mRNA for matrilin-3 | D | −20 | −8.92 | P | P | P | P | A | 7.61 | 3.73 | 3.14 | 6.45 | 1.46 |
| Cluster Incl. D87463:Human mRNA for KIAA0273 gene, complete cds | D | ~−27.0 | −8.9 | P | P | A | A | A | 2.4 | 1.89 | 0.7 | 1.71 | 1.28 |
| Cluster Incl. M65292:Human factor H homologue mRNA, complete cds | D | −6.5 | −8.71 | P | P | P | P | P | 8.7 | 8.8 | 6.7 | 6.47 | 3.29 |
| Cluster Incl. D86324:Homo sapiens mRNA for CMP-N-acetylneuraminic acid hydroxylase, complete cds | D | −8.3 | −8.24 | P | P | P | P | A | 8.06 | 6.69 | 3.79 | 3.19 | 2.44 |
| Cluster Incl. U80055:untitled cistine dioxygenase | D | −12.5 | −7.78 | P | P | P | P | P | 6.77 | 5.77 | 3.98 | 4.16 | 4.22 |
| D12485 Human mRNA for nucleotide pyrophosphatase, complete cds | D | −10.1 | −7.74 | P | P | P | P | P | 7.08 | 6.92 | 3.48 | 8.44 | 5.14 |
| Cluster Incl. W28729:50h2 Homo sapiens cDNA small nuclear RNA U2 | D | −13.8 | −7.36 | P | P | A | P | P | 5.41 | 4.51 | 0.83 | 2.69 | 2.37 |
| Cluster Incl. X90858:H. sapiens mRNA for uridine phosphorylase | MD | ~−20.1 | −7.01 | P | P | P | P | A | 3.72 | 5.21 | 2.83 | 2.45 | 0.86 |
| Cluster Incl. J04177:Human alpha-1 type XI collagen (COL11A1) mRNA, complete cds | D | −4.6 | −5.93 | P | P | P | P | P | 6.15 | 6.18 | 5.77 | 6.77 | 5.54 |
| Cluster Incl. AC003107:Human DNA from chromosome 19-specific cosmid R30064 containing the COMP gene, genomic sequence | D | −4.5 | −5.84 | P | P | P | P | P | 6.71 | 4.47 | 6.16 | 7.18 | 5.46 |
| D12485/FEATURE=cds#1/DEFINITION= HUMNPP Human mRNA for nucleotide pyrophosphatase, complete cds | D | −9.3 | −5.73 | P | P | P | P | P | 5.95 | 3.03 | 2.46 | 8.09 | 4.57 |
| Cluster Incl. AB006000:Homo sapiens mRNA for chondromodulin-I precursor, complete cds | D | ~−15.4 | −5.59 | P | P | A | P | A | 5.73 | 1.79 | 0.86 | 7 | −0.59 |
| Cluster Incl. X58288:H. sapiens hR-PTPu gene for protein tyrosine phosphatase | D | −11.4 | −5.52 | P | P | P | P | P | 5.87 | 6.65 | 3.66 | 4.53 | 5.19 |
| Cluster Incl. AF051160:Homo sapiens tyrosine phosphatase (PRL-1) gene, complete cds | D | ~−14.5 | −5.33 | P | P | M | P | P | 3.59 | 4.7 | 1.09 | 5.2 | 3.1 |
| X14787 Human mRNA for thrombospondin | D | −5.9 | −5.16 | P | P | P | P | P | 6.73 | 3.22 | 3.16 | 6.38 | 5.36 |
| Cluster Incl. J02611:Human apolipoprotein D mRNA, complete cds | D | ~−14.6 | −5.03 | P | P | A | A | A | 4.68 | 4.95 | 0.83 | 1.4 | −0.16 |
| S77154 beta-type transcription factor homolog [human, T lymphoid cell line, PEER, mRNA, 2469 nt] | D | ~−14.0 | −5.02 | P | P | A | P | A | 4.37 | 4.69 | 0.19 | 4.22 | −0.05 |
| S81914 radiation-inducible immediate-early gene [human, placenta, mRNA Partial, 1223 nt] | D | −5.2 | −4.93 | P | P | P | P | P | 7.32 | 5.01 | 4.61 | 7.51 | 4.9 |
| Cluster Incl. L13463:Human helix-loop-helix basic phosphoprotein (G0S8) mRNA, complete cds | D | −10.2 | −4.64 | P | P | P | P | P | 6.13 | 5.74 | 2.34 | 2.84 | 3.34 |
| J03910 Human (clone 14VS) metallothionein-IG (MT1G) gene, complete cds | D | −10.3 | −4.42 | P | P | A | P | A | 3.37 | 4.74 | 0.06 | 4.26 | 0.55 |
| Cluster Incl. AA224832:nc33b06.s1 Homo sapiens cDNA/len=447 | D | −5.5 | −4.41 | P | P | P | P | P | 4.69 | 4.74 | 2.47 | 5.54 | 3.12 |
| Cluster Incl. M69177:Human monoamine oxidase B (MAOB) mRNA, complete cds | D | −6.4 | −4.3 | P | P | P | P | A | 5.51 | 5.37 | 2.14 | 1.32 | 0.12 |
| Cluster Incl. M17017:Human beta-thromboglobulin-like protein mRNA, complete cds | D | ~−12.0 | −4.27 | P | P | A | P | P | 5.07 | 7.04 | 1.58 | 6.17 | 2.3 |

TABLE 2A-continued

RESULT OF MICRO ARRAY ANALYSIS: POSITIVE MARKERS
Positive markers: entries are ranked on sort score, the description column contains the Genbank Accession number and a short description of the protein encoded by it. The other column headers are explained above.

| Descriptions | Diff Call | P3-P0 Fold Change | P3-P0 Sort Score | Absolute call | | | | | log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| Cluster Incl. Y16241:*Homo sapiens* mRNA for nebulette | D | −6.5 | −4.11 | P | P | P | P | A | 7.01 | 7.45 | 3.24 | 5.46 | 1.57 |
| Cluster Incl. AF022375:*Homo sapiens* vascular endothelial growth factor mRNA, complete cds | D | −4.4 | −4.06 | P | P | P | P | P | 7.34 | 6.89 | 5.27 | 7.81 | 6.19 |
| Cluster Incl. AB003791:*Homo sapiens* mRNA for keratan sulfate Gal-6-sulfotransferase, complete cds | D | −8.2 | −3.84 | P | P | M | P | A | 4.26 | 5.78 | 1.02 | 3.62 | 0.13 |
| Cluster Incl. X00129:Human mRNA for retinol binding protein (RBP) | D | −3.8 | −3.73 | P | P | P | P | P | 8.12 | 8.11 | 6.84 | 8.38 | 7.91 |
| Cluster Incl. L26081:*Homo sapiens* semaphorin-III (Hsema-I) mRNA, complete cds | D | −5.5 | −3.66 | P | P | A | P | P | 6.77 | 5.31 | 1.78 | 2.73 | 3.62 |
| Cluster Incl. AA829286:of08a01.s1 *Homo sapiens* cDNA, 3 end | D | −7.3 | −3.66 | P | P | M | P | M | 5.68 | 6.2 | 1.24 | 2.92 | 1.11 |
| Cluster Incl. AF013512:untitled | D | −5.2 | −3.65 | P | P | P | P | A | 5.3 | 1.87 | 1.55 | 1.69 | 1.02 |
| Cluster Incl. L26336:Human heat shock protein HSPA2 gene, complete cds | D | −6.4 | −3.61 | P | P | P | P | P | 7.58 | 6.73 | 3.26 | 5.89 | 3.54 |
| Cluster Incl. U79273:Human clone 23933 mRNA sequence | D | −7.7 | −3.57 | P | P | P | P | P | 5.46 | 3.81 | 1.35 | 4 | 2.13 |
| Cluster Incl. M13509:Human skin collagenase mRNA, complete cds | D | −5.2 | −3.47 | P | P | P | P | P | 6.58 | 6.97 | 4.17 | 6.7 | 3.98 |
| Cluster Incl. AI762213:wi54d04.x1 *Homo sapiens* cDNA, 3 end | D | ~−10.4 | −3.42 | P | P | A | A | A | 4.89 | 5.52 | 0.8 | 1.31 | −0.59 |
| Cluster Incl. M63978:Human vascular endothelial growth factor gene | D | −7.4 | −3.4 | P | P | P | P | P | 5.39 | 4.3 | 2.9 | 6.21 | 3.46 |
| Cluster Incl. L19314:Human HRY gene, complete cds | D | −5.3 | −3.38 | P | P | P | P | P | 5.52 | 5.23 | 2.94 | 4.75 | 2.21 |
| Cluster Incl. AL080172:*Homo sapiens* mRNA; cDNA DKFZp434G231 (from clone DKFZp434G231) | MD | ~−11.1 | −3.35 | P | P | P | P | P | 3.52 | 3.67 | 2.49 | 3.94 | 3.31 |
| Cluster Incl. X04470:Human mRNA for antileukoprotease (ALP) from cervix uterus | D | −4 | −3.31 | P | P | P | P | P | 6.68 | 6.19 | 3.15 | 5.46 | 2.36 |
| Cluster Incl. X07834:Human mRNA for manganese superoxide dismutase (EC 1.15.1.1) | D | −5.6 | −3.23 | P | P | P | P | P | 6.82 | 5.82 | 2.05 | 4.46 | 4.02 |
| U41068 Human collagen alpha2(XI) (COL11A2) gene, exons 61 and 62, and partial cds | NC | −8.2 | −3.17 | P | P | A | A | A | 2.84 | 2.04 | 0.61 | 2.24 | 0.37 |
| Cluster Incl. AW006742:wr28g10.x1 *Homo sapiens* cDNA, 3 end | D | −7.1 | −3.13 | P | P | P | P | P | 5.38 | 4.03 | 1.8 | 4.58 | 4.85 |
| Cluster Incl. AB023194:*Homo sapiens* mRNA for KIAA0977 protein, complete cds | D | −7.4 | −2.99 | P | P | A | P | P | 4.66 | 3.19 | 0.58 | 3.44 | 3.26 |
| AF024710/FEATURE=/DEFINITION=AF024710 *Homo sapiens* vascular endothelial growth factor (VEGF) mRNA, 3 UTR | D | −3.5 | −2.88 | P | P | P | P | P | 7.53 | 7.25 | 5.78 | 6.99 | 5.3 |
| L11672/FEATURE=/DEFINITION=HUMKRUPZN Human Kruppel related zinc finger protein (HTF10) mRNA, complete cds | D | −4.4 | −2.84 | P | P | P | P | P | 8.56 | 7.38 | 4.55 | 6.7 | 7.1 |
| Cluster Incl. AF000984:*Homo sapiens* dead box, Y isoform (DBY) mRNA, alternative transcript 2, complete cds | D | −5.7 | −2.83 | P | P | P | P | P | 8.35 | 9.18 | 4.57 | 8.44 | 7.18 |
| Cluster Incl. U91512:Human adhesion molecule ninjurin mRNA, complete cds | D | −6.7 | −2.83 | P | P | A | P | P | 3.1 | 3.49 | 0.68 | 3.05 | 1.79 |
| Cluster Incl. Z46629:*Homo sapiens* SOX9 mRNA | D | −4.7 | −2.79 | P | P | P | P | P | 6.8 | 7.6 | 3.72 | 7.49 | 4.73 |
| D87119/FEATURE=/DEFINITION=D87119 *Homo sapiens* mRNA for GS3955, complete cds | D | −4.5 | −2.78 | P | P | P | P | P | 6.88 | 4.62 | 3.06 | 5.17 | 3.66 |
| Cluster Incl. S95936:transferrin [human, liver, mRNA, 2347 nt]/cds=(79,2175) | D | ~−8.8 | −2.77 | P | P | M | A | A | 5.68 | 6.14 | 1.19 | 1.64 | 1.62 |
| Cluster Incl. L49169:Human G0S3 mRNA, complete cds | D | −3.5 | −2.73 | P | P | P | P | P | 5.31 | 5.57 | 4.18 | 5.41 | 3.91 |
| Cluster Incl. Y17448:*Homo sapiens* CCBL1 gene, last two exons | NC | ~−8.8 | −2.72 | P | P | M | P | P | 1.32 | 1.01 | 0.99 | 1.9 | 1.43 |
| M61906/FEATURE=/DEFINITION=HUMP13KIN Human P13-kinase associated p85 mRNA sequence | D | ~−8.6 | −2.69 | P | P | A | P | P | 6.4 | 4.58 | 2.01 | 4.37 | 3.05 |
| U67156/FEATURE=/DEFINITION=HSU67156 Human mitogen-activated kinase kinase kinase 5 (MAPKKK5) mRNA, complete cds | D | −6.2 | −2.6 | P | P | P | P | P | 7.31 | 5 | 2.56 | 5.54 | 4.62 |
| Cluster Incl. M72393:Human calcium-dependent phospholipid-binding protein (PLA2) mRNA, complete cds | D | ~−8.3 | −2.57 | P | P | P | A | P | 6.5 | 8.06 | 1.28 | 6.83 | 5.26 |
| Cluster Incl. AI189287:qd05c04.x1 *Homo sapiens* cDNA, 3 end | D | ~−8.4 | −2.55 | P | P | A | A | A | 3.47 | 5.97 | 0.67 | 1.48 | 0.72 |
| Cluster Incl. W27541:32c12 *Homo sapiens* cDNA | D | ~−8.6 | −2.53 | P | P | A | P | P | 2.58 | 3.38 | 0.96 | 3.71 | 1.2 |

TABLE 2A-continued

RESULT OF MICRO ARRAY ANALYSIS: POSITIVE MARKERS
Positive markers: entries are ranked on sort score, the description column contains the Genbank Accession number and a short description of the protein encoded by it. The other column headers are explained above.

| Descriptions | Diff Call | P3-P0 Fold Change | P3-P0 Sort Score | Absolute call | | | | | log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| M19154/FEATURE=mRNA/Human transforming growth factor-beta-2 mRNA, complete cds | D | −5.9 | −2.5 | P | P | P | P | P | 5.88 | 5.61 | 2.05 | 6.26 | 3.58 |
| Cluster Incl. W26496:30d2 *Homo sapiens* cDNA | D | −3.1 | −2.48 | P | P | P | P | P | 9.04 | 7.55 | 7.1 | 9.18 | 7.22 |
| Cluster Incl. AI953789:wx69d10.x1 *Homo sapiens* cDNA, 3 end | D | −4 | −2.41 | P | P | P | P | P | 6.43 | 4.88 | 1.82 | 2.44 | 2.33 |
| U48807/FEATURE=/DEFINITION=HSU48807 Human MAP kinase phosphatase (MKP-2) mRNA, complete cds | D | ~−8.0 | −2.4 | P | P | A | P | P | 4.9 | 6.81 | 2.04 | 1.59 | 2.65 |
| Cluster Incl. X51405:Human mRNA for carboxypeptidase E (EC 3.4.17.10) | D | −4 | −2.35 | P | P | P | P | P | 8.2 | 5.9 | 5.38 | 7.72 | 2.56 |
| Cluster Incl. D64137:Human KIP2 gene for Cdk-inhibitor p57KIP2, complete cds | D | ~−8.5 | −2.13 | P | P | A | A | A | 3.42 | 2.09 | −0.12 | 0.65 | 0.94 |
| Cluster Incl. AI768188:wg82b12.x1 *Homo sapiens* cDNA, 3 end | D | −4.5 | −2.1 | P | P | P | P | P | 7.61 | 8.83 | 3.03 | 7.84 | 7.17 |
| L26336/FEATURE=cds/DEFINITION= HUMHSPA2A Human heat shock protein HSPA2 gene, complete cds | D | −6.6 | −2.01 | P | P | M | P | A | 4.03 | 2.31 | 1.02 | 3.5 | 1.33 |
| M87770/FEATURE=/DEFINITION=HUMKSAMI Human fibroblast growth factor receptor (K-sam) mRNA, complete cds | D | −3.6 | −1.99 | P | P | P | P | P | 6.88 | 4.46 | 4.11 | 5.81 | 3.58 |
| Cluster Incl. AB015228:*Homo sapiens* mRNA for RALDH2-T, complete cds | D | −4.7 | −1.97 | P | P | A | A | A | 4.67 | 4.43 | 1 | 2.51 | 0.78 |
| Cluster Incl. Y10313:*Homo sapiens* mRNA IFRD1 (PC4) interferon-related developmental regulator | D | −4.4 | −1.96 | P | P | P | P | P | 8.71 | 7.36 | 5.37 | 6.52 | 6.45 |
| U04840/FEATURE=/DEFINITION=HSU04840 Human onconeural ventral antigen-1 (Nova-1) mRNA, complete cds | D | −5.6 | −1.95 | P | P | M | P | A | 3.57 | 4.44 | 1.26 | 2.74 | 1.77 |
| Cluster Incl. AB007903:*Homo sapiens* KIAA0443 mRNA, complete cds | D | −5.1 | −1.94 | P | P | P | P | P | 4.66 | 3.75 | 2.38 | 3.01 | 2.92 |
| Cluster Incl. J04513:Human basic fibroblast growth factor (bFGF) 22.5 kd, 21 kd and 18 kd protein mRNA, complete cds | D | ~−7.2 | −1.87 | P | P | A | P | P | 3.09 | 6.09 | 2.23 | 1.66 | 2.26 |
| Cluster Incl. D87119:*Homo sapiens* mRNA for GS3955, complete cds | D | −3.1 | −1.86 | P | P | P | P | P | 6.09 | 4.73 | 3.32 | 5.45 | 3.63 |
| Cluster Incl. AA524547:ng45h04.s1 *Homo sapiens* cDNA, 3 end | D | ~−7.1 | −1.82 | P | P | A | A | A | 3.63 | 4.58 | 1.19 | 2.26 | 2.01 |
| Cluster Incl. U88629:Human RNA polymerase II elongation factor ELL2, complete cds | D | −4.1 | −1.8 | P | P | P | P | P | 7.18 | 6.37 | 4.29 | 5.47 | 4.41 |
| Cluster Incl. M59499:Human lipoprotein-associated coagulation inhibitor (LACI) gene | D | −4.2 | −1.79 | P | P | P | P | P | 6.64 | 6.9 | 2.8 | 6.22 | 6.74 |
| Cluster Incl. U93181:*Homo sapiens* nuclear dual-specificity phosphatase (SBF1) mRNA, partial cds | MD | −5.9 | −1.79 | P | P | P | P | P | 1.74 | 1.17 | 1.32 | 1.37 | 1.35 |
| Cluster Incl. AB020657:*Homo sapiens* mRNA for KIAA0850 protein, complete cds | D | −4.1 | −1.78 | P | P | M | P | P | 6.26 | 7.21 | 1.28 | 5.44 | 3.96 |
| Cluster Incl. AL050275:*Homo sapiens* mRNA; cDNA DKFZp566D213 (from clone DKFZp566D213) | D | ~−6.9 | −1.77 | P | P | A | P | P | 1.7 | 1.32 | 0.7 | 2.14 | 1.49 |
| Cluster Incl. X17406:Human mRNA for cartilage specific proteoglycan | D | −2.5 | −1.75 | P | P | P | P | P | 5.7 | 5.54 | 5.35 | 5.85 | 4.35 |
| Cluster Incl. AF049884:*Homo sapiens* Arg/Abl-interacting protein ArgBP2a (ArgBP2a) mRNA, complete cds | D | −4.7 | −1.73 | P | P | P | P | P | 6.05 | 1.48 | 1.87 | 1.97 | 1.75 |
| Cluster Incl. AC004774:*Homo sapiens* BAC clone RG300E22 from 7q21-q31.1 | D | −6.2 | −1.7 | P | P | P | P | A | 3.73 | 2.38 | 3.58 | 3.37 | 2.97 |
| X68742/FEATURE=/DEFINITION=HSINTASA *H. sapiens* mRNA for integrin, alpha subunit | D | −3.9 | −1.69 | P | P | P | P | P | 6.84 | 6.91 | 3.38 | 4.98 | 3.31 |
| Cluster Incl. U72206:Human guanine nucleotide regulatory factor (LFP40) mRNA, complete cds | D | −3.8 | −1.69 | P | P | P | P | P | 4.73 | 2.86 | 2.53 | 3.65 | 3.51 |
| Cluster Incl. AL050290:*Homo sapiens* mRNA; cDNA DKFZp586G1923 (from clone DKFZp586G1923) | D | −2.8 | −1.68 | P | P | P | P | P | 9.12 | 8.67 | 7.33 | 9.07 | 5.68 |
| Cluster Incl. D15050:Human mRNA for transcription factor AREB6, complete cds | D | −5.8 | −1.68 | P | P | P | P | M | 4.69 | 6.84 | 1.45 | 3.12 | 0.91 |
| Fibroblast Growth Factor Receptor K-Sam, Alt. Splice 3, K-Sam III | D | −4.2 | −1.67 | P | P | P | P | P | 5.68 | 3.67 | 2.72 | 4.51 | 4.16 |
| Cluster Incl. X06882:Human gene for CD14 differentiation antigen | MD | −4.4 | −1.66 | P | P | P | A | A | 2.48 | 1.95 | 1.26 | 0.84 | 0.02 |

TABLE 2A-continued

RESULT OF MICRO ARRAY ANALYSIS: POSITIVE MARKERS
Positive markers: entries are ranked on sort score, the description column contains the Genbank Accession number and a short description of the protein encoded by it. The other column headers are explained above.

| Descriptions | Diff Call | P3-P0 Fold Change | P3-P0 Sort Score | Absolute call | | | | | log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| Cluster Incl. AL080190:*Homo sapiens* mRNA; cDNA DKFZp434A202 (from clone DKFZp434A202) | NC | ~-7.5 | -1.65 | P | P | P | P | M | 3.92 | 3.73 | 1.87 | 2.18 | 1.1 |
| Cluster Incl. D42040:Human mRNA for KIAA9001 gene, complete cds | D | -3.7 | -1.64 | P | P | P | P | P | 4.52 | 5.39 | 2.14 | 4.51 | 4.79 |
| X52541/FEATURE=cds/DEFINITION=HSEGR1 Human mRNA for early growth response protein 1 (hEGR1) | D | -3.6 | -1.63 | P | P | P | P | P | 4.35 | 4.1 | 2.57 | 3.71 | 3.99 |
| Cluster Incl. X67098:*H. sapiens* rTS alpha mRNA containing four open reading frames | D | -3.5 | -1.62 | P | P | P | P | A | 6.1 | 4.44 | 4.04 | 4.12 | 1.29 |
| Cluster Incl. M31516:Human decay-accelerating factor mRNA, complete cds | D | -4.1 | -1.61 | P | P | P | P | P | 6.98 | 8.13 | 4.22 | 4.69 | 2.39 |
| Cluster Incl. AB004066:*Homo sapiens* mRNA for DEC1, complete cds | D | -3.1 | -1.59 | P | P | P | P | P | 7.34 | 7.76 | 4.87 | 7.91 | 3.9 |
| Cluster Incl. AB020659:*Homo sapiens* mRNA for KIAA0852 protein, complete cds | D | -5.4 | -1.53 | P | P | A | P | P | 3.46 | 3.8 | 1.69 | 3.03 | 3 |
| Cluster Incl. X17042:Human mRNA for hematopoetic proteoglycan core protein | D | -3.3 | -1.51 | P | P | P | P | P | 9.29 | 8.56 | 5.67 | 8.31 | 6.62 |
| Cluster Incl. U14550:Human sialyltransferase SThM (sthm) mRNA, complete cds | D | -5.3 | -1.51 | P | P | A | A | P | 3.49 | 2.93 | 0.95 | 0.22 | 1.16 |
| Cluster Incl. AJ222700:*Homo sapiens* mRNA for TSC-22 protein | D | -3.2 | -1.48 | P | P | P | P | P | 8.91 | 8.47 | 5.75 | 8.04 | 8.44 |
| Y00083/FEATURE=cds/DEFINITION=HSGTSF Human mRNA for glioblastoma-derived T-cell suppressor factor G-TsF (transforming growth factor-beta2, TGF-beta2) | D | ~-7.0 | -1.48 | P | P | A | P | P | 3.64 | 2.51 | -0.62 | 5.17 | 3.13 |
| L15388/FEATURE=/DEFINITION=HUMGRK5A Human G protein-coupled receptor kinase (GRK5) mRNA, complete cds | D | -4 | -1.47 | P | P | P | P | P | 4.92 | 6.25 | 2.45 | 3.68 | 4.14 |
| Z71929/FEATURE=cds/DEFINITION= HSFGFR2MR *H. sapiens* FGFR2 mRNA | D | -3 | -1.45 | P | P | P | P | P | 6.02 | 1.29 | 3.76 | 5.29 | 2.19 |
| Cluster Incl. AF091071:*Homo sapiens* clone 192 Rer1 mRNA, complete | NC | ~-6.0 | -1.43 | P | P | A | P | P | 3.15 | 1.92 | 2.54 | 3.74 | 3.13 |
| Cluster Incl. U72649:Human BTG2 (BTG2) mRNA, complete cds | D | -2.9 | -1.42 | P | P | P | P | P | 6.68 | 7.3 | 3.7 | 4.67 | 5.34 |
| Cluster Incl. AF009801:*Homo sapiens* homeodomain protein (BAPX1) mRNA, complete cds | D | -4.1 | -1.42 | P | P | P | P | A | 4.12 | 3.64 | 2.2 | 2.1 | -0.1 |
| Cluster Incl. M64347:Human novel growth factor receptor mRNA, 3 cds | D | -5.1 | -1.42 | P | P | A | P | A | 3.84 | 3.29 | 0.55 | 4.21 | 0.54 |
| Cluster Incl. J03037:Human carbonic anhydrase II mRNA, complete cds | D | ~-6.1 | -1.41 | P | P | A | P | P | 4.65 | 2.92 | -0.11 | 6.47 | 3.72 |
| U14394/FEATURE=/DEFINITION=HSU14394 Human tissue inhibitor of metalloproteinases-3 mRNA, complete cds | D | 2.6 | -1.39 | P | P | P | P | P | 6.14 | 5.95 | 3.48 | 6.79 | 6.04 |
| Cluster Incl. X69090:*H. sapiens* mRNA for skeletal muscle 190 kD protein | NC | ~-5.8 | -1.39 | P | P | A | A | A | 1.99 | 1.51 | 1.22 | 0.41 | 1.85 |
| Cluster Incl. Y15801:*Homo sapiens* mRNA for PRKY protein | D | -4.8 | -1.36 | P | P | P | P | P | 4.58 | 3.9 | 2.05 | 3.23 | 3.91 |
| Cluster Incl. AF035318:*Homo sapiens* clone 23705 mRNA sequence | NC | -3.9 | -1.36 | P | P | P | A | A | 4.25 | 2.91 | 1.81 | 2.87 | 1.81 |
| Cluster Incl. L13972:*Homo sapiens* beta-galactoside alpha-2,3-sialyltransferase (SIAT4A) mRNA, complete cds | D | ~-5.8 | -1.34 | P | P | A | P | A | 1.33 | 3.2 | -0.12 | 1.43 | 0.18 |
| Cluster Incl. M62831:Human transcription factor ETR101 mRNA, complete cds | D | -2.2 | -1.33 | P | P | P | P | P | 6.74 | 5.8 | 6.09 | 6.53 | 6.3 |
| Cluster Incl. AF098462:*Homo sapiens* stanniocalcin-related protein mRNA, complete cds | D | -2.8 | -1.33 | P | P | P | P | P | 5.41 | 1.93 | 3.22 | 3.46 | 3.99 |
| Cluster Incl. X89602:*H. sapiens* mRNA for rTS beta protein | D | ~-5.6 | -1.32 | P | P | A | P | A | 3.2 | 2.4 | 0.3 | 1.59 | 0.36 |
| Cluster Incl. AB014551:*Homo sapiens* mRNA for KIAA0651 protein, complete cds | D | -3.2 | -1.31 | P | P | P | P | P | 4.63 | 5.62 | 2.8 | 4.42 | 3.92 |
| Cluster Incl. AJ223321:*Homo sapiens* RP58 gene, complete CDS | D | ~-5.7 | -1.31 | P | P | A | P | P | 4.65 | 7.28 | 0.68 | 3.64 | 3.62 |
| Cluster Incl. X04430:Human IFN-beta 2a mRNA for interferon-beta-2 | D | -3.2 | -1.29 | P | P | P | P | P | 6.3 | 7.61 | 4.18 | 8.13 | 4.11 |
| Cluster Incl. D31887:Human mRNA for KIAA0062 gene, partial cds | D | -2.1 | -1.28 | P | P | P | P | P | 7.84 | 4.68 | 7.06 | 7.87 | 6.1 |
| Cluster Incl. M69199:Human G0S2 protein gene, complete cds | D | -3.3 | -1.28 | P | P | P | P | P | 4.99 | 5.32 | 3.13 | 7.04 | 2.07 |

TABLE 2A-continued

RESULT OF MICRO ARRAY ANALYSIS: POSITIVE MARKERS
Positive markers: entries are ranked on sort score, the description column contains the Genbank Accession number and a short description of the protein encoded by it. The other column headers are explained above.

| Descriptions | Diff Call | P3-P0 Fold Change | P3-P0 Sort Score | Absolute call | | | | | log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| Cluster Incl. AB020648:*Homo sapiens* mRNA for KIAA0841 protein, partial cds | NC | −4.3 | −1.28 | P | P | P | P | P | 2.65 | 1.1 | 1.99 | 2.12 | 2.97 |
| Cluster Incl. AL022723:dJ377H14.9 (major histocompatibility complex, class I, F (CDA12)) | D | −3.3 | −1.28 | P | P | P | P | A | 4.72 | 5.69 | 1.87 | 3.33 | 1.63 |
| Cluster Incl. U00115:Human zinc-finger protein (bcl-6) mRNA, complete cds | D | −2.7 | −1.27 | P | P | P | P | P | 8.33 | 8.15 | 6.67 | 6.88 | 5.37 |
| Cluster Incl. U52191:Human SMCY (H-Y) mRNA, complete cds | NC | −5.3 | −1.25 | P | P | M | P | P | 2.78 | 4.64 | 1.14 | 2.73 | 2.05 |

TABLE 2B

RESULT OF MICRO ARRAY ANALYSIS: NEGATIVE MARKERS
Negative markers: entries are ranked on sort score, the description column contains the Genbank Accession number and a short description of the protein encoded by it. The other column headers are explained at the beginning of table 1.

| Descriptions | Diff Call | P3-P0 Fold Change | P3-P0 Sort Score | Absolute call | | | | | Log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| U50648/FEATURE=mRNA/DEFINITION= HSIIPKR17 Human interferon-inducible RNA-dependent protein kinase (Pkr) gene, exon 17 and complete cds | I | 10.4 | 10.63 | P | P | P | P | P | 2.15 | 3.35 | 4.58 | 3.91 | 2.67 |
| Cluster Incl. AL050025:*Homo sapiens* mRNA; cDNA DKFZp564D066 (from clone DKFZp564D066) | I | 8.7 | 9.52 | A | P | P | P | P | 5 | 2.14 | 6.52 | 5.97 | 6.72 |
| Cluster Incl. AF001691:*Homo sapiens* 195 kDa cornified envelope precursor mRNA, complete cds | I | ~21.3 | 8.26 | A | P | P | A | P | 1.43 | 0.34 | 3.99 | 0.64 | 3.29 |
| Cluster Incl. J04599:Human hPGI mRNA encoding bone small proteoglycan I (biglycan), complete cds | I | 5.8 | 7.75 | A | A | P | P | P | 0.49 | 0.95 | 2.67 | 2.06 | 3.43 |
| Cluster Incl. X64559:*H. sapiens* mRNA for tetranectin | I | 5.5 | 7.32 | P | P | P | P | P | 4.23 | 1.46 | 5.9 | 4.37 | 6.01 |
| J03779/FEATURE=mRNA/DEFINITION= HUMCALLA Human common acute lymphoblastic leukemia antigen (CALLA) mRNA, complete cds | I | 10 | 7.15 | A | A | P | A | A | 0.27 | 0.89 | 3.54 | 1.21 | 0.62 |
| M65188/FEATURE=/DEFINITION=HUMCX43 Human connexin 43 (GJA1, Cx43) mRNA, complete cds | I | ~18.2 | 6.53 | A | A | P | P | P | 2.31 | −0.3 | 3.76 | 3.68 | 2.79 |
| Cluster Incl. AB017563:*Homo sapiens* IGSF4 gene | I | 10.9 | 6.47 | A | P | P | P | P | 3.4 | 1.82 | 5.49 | 4.8 | 3.96 |
| Cluster Incl. AF037335:*Homo sapiens* carbonic anhydrase precursor (CA 12) mRNA, complete cds | I | 7.1 | 6.37 | P | P | P | P | P | 5.33 | 1.01 | 7.28 | 7.3 | 6.86 |
| X82153/FEATURE=cds/DEFINITION= HSOC2RNA *H. sapiens* mRNA for cathepsin O | I | 6.2 | 6.13 | A | P | P | P | P | 4.57 | 1.1 | 6.6 | 2.24 | 4.5 |
| Cluster Incl. U29953:Human pigment epithelium-derived factor gene, complete cds | I | 6.6 | 6 | A | P | P | P | P | 1.91 | 0.57 | 4.19 | 3.26 | 4.57 |
| X82153/FEATURE=cds/DEFINITION= HSOC2RNA *H. sapiens* mRNA for cathepsin O | I | 5.6 | 5.92 | P | P | P | P | P | 5.42 | 1.57 | 7.43 | 3.02 | 5.66 |
| Cluster Incl. AI660656:wf23c07.x1 *Homo sapiens* cDNA, 3 end | I | ~14.9 | 5.56 | A | A | P | A | P | 1.84 | −0.3 | 5.8 | 1.75 | 4.84 |
| Cluster Incl. U20982:Human insulin-like growth factor binding protein-4 (IGFBP4) gene, promoter and complete cds | I | 4.1 | 5.37 | P | P | P | P | P | 3.17 | 4.46 | 5.34 | 3.45 | 3.2 |
| Cluster Incl. M25915:Human complement cytolysis inhibitor (CLI) mRNA, complete cds | I | 3.6 | 4.86 | A | P | P | P | P | 1.63 | 0.42 | 4.81 | 6.48 | 3.3 |
| Cluster Incl. U15979:Human (dlk) mRNA, complete cds | I | ~12.9 | 4.64 | M | A | P | P | P | 0.96 | 1.21 | 3.67 | 2.65 | 1.69 |
| Neurofibromatosis 2 Tumor Suppressor | I | 7.7 | 4.6 | P | P | P | P | P | 1.27 | 1.79 | 3.68 | 2.23 | 3.01 |
| Cluster Incl. X82153:*H. sapiens* mRNA for cathepsin O | I | 4.5 | 4.55 | P | P | P | P | P | 7.23 | 5.58 | 8.51 | 6.64 | 7.73 |
| Cluster Incl. AF039656:*Homo sapiens* neuronal tissue-enriched acidic protein (NAP-22) mRNA, complete cds | I | 3.6 | 3.95 | P | P | P | P | P | 7.39 | 2 | 8.29 | 8.24 | 8.14 |
| Cluster Incl. U48959:*Homo sapiens* myosin light chain kinase (MLCK) mRNA, complete cds | I | 4.3 | 3.74 | A | P | P | P | P | 5.12 | −0.4 | 6.61 | 4.55 | 5.97 |
| Cluster Incl. L26232:Human phospholipid transfer protein mRNA, complete cds | I | 4.2 | 3.53 | P | P | P | P | P | 5.51 | 2.66 | 6.41 | 5.57 | 4.89 |

TABLE 2B-continued

RESULT OF MICRO ARRAY ANALYSIS: NEGATIVE MARKERS
Negative markers: entries are ranked on sort score, the description column contains the Genbank Accession number and a short description of the protein encoded by it. The other column headers are explained at the beginning of table 1.

| Descriptions | Diff Call | P3-P0 Fold Change | P3-P0 Sort Score | Absolute call | | | | | Log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| Cluster Incl. X16832:Human mRNA for cathepsin H (EC 3.4.22.16) | I | 6.3 | 3.31 | A | P | P | P | P | 2.55 | 1.37 | 4.34 | 2.68 | 3.32 |
| Cluster Incl. U24389:Human lysyl oxidase-like protein gene | I | 3.3 | 3.16 | A | P | P | P | P | 5.59 | 2.17 | 5.37 | 6.12 | 5.34 |
| Cluster Incl. M34175:Human beta adaptin mRNA, complete cds | I | 6 | 3.07 | P | P | P | P | P | 3.28 | 5.04 | 3.99 | 4.77 | 4.45 |
| Cluster Incl. U59321:Human DEAD-box protein p72 (P72) mRNA, complete cds | MI | ~9.7 | 3.06 | P | P | P | P | A | 1.46 | 1.62 | 2.45 | 2.67 | 1.38 |
| U43142/FEATURE=/DEFINITION=HSU43142 Human vascular endothelial growth factor related protein VRP mRNA, complete cds | I | 6.4 | 2.98 | A | P | P | P | P | 2.26 | −0.2 | 3.21 | 6.82 | 5.15 |
| Cluster Incl. AF009314:Homo sapiens clone TUA8 Cri-du-chat region mRNA | I | 5.8 | 2.95 | A | M | P | P | P | 1.21 | 1.43 | 4.85 | 3.1 | 4.49 |
| Cluster Incl. U18420:Human ras-related small GTP binding protein Rab5 (rab5) mRNA, complete cds | I | 4.4 | 2.94 | P | P | P | P | P | 3.68 | 5.64 | 5.44 | 4.68 | 4.16 |
| Cluster Incl. AL080181:Homo sapiens mRNA; cDNA DKFZp434O111 (from clone DKFZp434O111) | I | 6.1 | 2.94 | M | P | P | P | P | 3.14 | 1.17 | 4.81 | 4.23 | 4.18 |
| Cluster Incl. M94345:Homo sapiens macrophage capping protein mRNA, complete cds | I | 3.3 | 2.82 | P | P | P | P | P | 5.1 | 3.9 | 5.64 | 5.27 | 5.44 |
| Cluster Incl. U52153:Human inwardly rectifying potassium channel Kir3.2 mRNA, complete cds | I | ~8.9 | 2.82 | A | A | P | A | A | 0.67 | 0.07 | 4.46 | 0.18 | −0.3 |
| Cluster Incl. D28124:Human mRNA for unknown product, complete cds | I | 3.1 | 2.7 | P | P | P | P | P | 3.84 | 3.36 | 4.61 | 4.31 | 4.68 |
| Cluster Incl. U19718:Human microfibril-associated glycoprotein (MFAP2) mRNA, complete cds | I | 3.3 | 2.67 | P | P | P | P | P | 4.37 | 2.02 | 4.85 | 5.33 | 4.88 |
| Cluster Incl. X01703:Human gene for alpha-tubulin (b alpha 1) | I | 3 | 2.64 | P | P | P | P | P | 7.98 | 7.43 | 8.8 | 9.23 | 8.61 |
| Cluster Incl. U52840:Homo sapiens semaphorin F homolog mRNA, complete cds | I | ~17.1 | 2.6 | A | A | P | A | A | 0.37 | 0.2 | 2.28 | 1.29 | 1.29 |
| Cluster Incl. U53445:Human ovarian cancer down-regulated myosin heavy chain homolog (Doc1) mRNA, complete cds | I | 7.4 | 2.56 | A | A | P | A | P | 1.66 | 0.01 | 3.41 | 1.32 | 5.63 |
| Cluster Incl. AF051321:Homo sapiens Sam68-like phosphotyrosine protein alpha (SALP) mRNA, complete cds | I | ~8.4 | 2.47 | P | A | P | P | P | 1.54 | 2.89 | 5.35 | 4.14 | 2.94 |
| Cluster Incl. AA675900:g02504r Homo sapiens cDNA, 5 end | MI | ~7.9 | 2.39 | P | A | P | P | P | 1.09 | 2.26 | 1.27 | 3.08 | 2.15 |
| Cluster Incl. D14657:Human mRNA for KIAA0101 gene, complete cds | NC | ~8.2 | 2.38 | A | P | P | P | P | 3.24 | 0.38 | 3.43 | 6.85 | 5.28 |
| Cluster Incl. AI701156:we10f09.x1 Homo sapiens cDNA, 3 end | I | ~8.1 | 2.36 | A | A | P | P | A | 0.28 | 0.93 | 2 | 2.21 | 2.04 |
| U27185/FEATURE=/DEFINITION=HSU27185 Human RAR-responsive (TIG1) mRNA, complete cds | I | 6.3 | 2.33 | A | P | P | P | P | 1.94 | −0.5 | 3.87 | 2.74 | 2.26 |
| Cluster Incl. M13560:Human Ia-associated invariant gamma-chain gene | I | ~8.0 | 2.31 | P | P | P | P | P | 1.17 | 2.95 | 2.9 | 2.34 | 2.15 |
| Cluster Incl. X76534:H. sapiens NMB mRNA | I | 3 | 2.27 | P | P | P | P | P | 7.96 | 2.14 | 8.38 | 6.91 | 8.27 |
| Cluster Incl. U30521:Human P311 HUM (3.1) mRNA, complete cds | I | 2.9 | 2.23 | P | P | P | P | P | 6.43 | 7.32 | 7.54 | 7.24 | 6.65 |
| Cluster Incl. M55531:Human glucose transport-like 5 (GLUT5) mRNA, complete cds | I | ~7.6 | 2.2 | A | A | P | A | P | 0.55 | −0.3 | 2.68 | −0.11 | 1.05 |
| J04164/FEATURE=/DEFINITION=HUM927A Human interferon-inducible protein 9-27 mRNA, complete cds | MI | 2.8 | 2.2 | P | A | P | P | P | 1.23 | 3.78 | 2.46 | 2.47 | 2.68 |
| Cluster Incl. M10905:Human cellular fibronectin mRNA | I | 2.5 | 2.18 | P | P | P | P | P | 3.45 | 3.26 | 5.26 | 3.34 | 3.26 |
| Cluster Incl. AB002305:Human mRNA for KIAA0307 gene, complete cds | I | 4.6 | 2.18 | P | P | P | P | P | 4.74 | 1.33 | 5.24 | 4.38 | 4.38 |
| Cluster Incl. AF015257:Homo sapiens flow-induced endothelial G protein-coupled receptor (FEG-1) mRNA, complete cds | I | ~7.9 | 2.18 | A | P | P | P | P | 1.25 | 0.59 | 3.48 | 2.39 | 3.7 |
| D28364/FEATURE=/DEFINITION=HUMAI23 Human mRNA for annexin II, 5 UTR (sequence from the 5 cap to the start codon) | I | 4.2 | 2.17 | P | P | P | P | P | 4.53 | 5.85 | 6.32 | 7.63 | 6.89 |
| Cluster Incl. U27768:Human RGP4 mRNA, complete cds | I | ~7.7 | 2.16 | P | A | P | P | P | −0.3 | 1.67 | 3.37 | 4.39 | 3.85 |
| X67325/FEATURE=cds/DEFINITION=HSP27 H. sapiens p27 mRNA | NC | 6.3 | 2.11 | A | A | P | A | A | 1.59 | 0.2 | 1.88 | 0.57 | −1.03 |

TABLE 2B-continued

RESULT OF MICRO ARRAY ANALYSIS: NEGATIVE MARKERS
Negative markers: entries are ranked on sort score, the description column contains the Genbank Accession number and a short description of the protein encoded by it. The other column headers are explained at the beginning of table 1.

| Descriptions | Diff Call | P3-P0 Fold Change | P3-P0 Sort Score | Absolute call | | | | | Log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| Cluster Incl. X74331:*H. sapiens* mRNA for DNA primase (subunit p58) | I | 4.9 | 2.06 | P | P | P | P | P | 2.18 | 2.42 | 4.18 | 4.8 | 5.14 |
| Cluster Incl. AI887421:wm05c01.x1 *Homo sapiens* cDNA, 3 end | I | 6.7 | 2.04 | A | A | P | P | P | 0.59 | 1.06 | 2.55 | 1.18 | 1.83 |
| Cluster Incl. M22324:Human aminopeptidase N/CD13 mRNA encoding aminopeptidase N, complete cds | I | 4.1 | 2 | A | A | P | P | P | 1.91 | 0.35 | 4.37 | 4.96 | 4.64 |
| Cluster Incl. AF032906:*Homo sapiens* cathepsin Z precursor (CTSZ) mRNA, complete cds | I | 6.3 | 2 | P | P | P | P | P | 0.98 | 2.5 | 2.81 | 1.9 | 2.24 |
| Cluster Incl. AF005392:*Homo sapiens* alpha tubulin (TUBA2) gene, partial cds | NC | 3.4 | 1.93 | A | P | P | P | A | 2.94 | 3.76 | 2.78 | 4.04 | 2.73 |
| Cluster Incl. X99268:*H. sapiens* mRNA for B-HLH DNA binding protein | I | 3.4 | 1.9 | P | P | P | P | P | 3.8 | 4.22 | 5.55 | 6.49 | 5.42 |
| Cluster Incl. AF059214:*Homo sapiens* cholesterol 25-hydroxylase mRNA, complete cds | I | 4.5 | 1.88 | A | P | P | P | P | 2.78 | −1.1 | 5.96 | 7.14 | 5.91 |
| Cluster Incl. X60708:Human pcHDP7 mRNA for liver dipeptidyl peptidase IV | I | 5.9 | 1.87 | A | P | P | P | P | 2.83 | 0.48 | 5.2 | 4.66 | 5.35 |
| Cluster Incl. D83198:*Homo sapiens* mRNA expressed in thyroid gland | I | 3.2 | 1.84 | P | P | P | P | P | 4.46 | 3.14 | 5.01 | 5.25 | 5.36 |
| Cluster Incl. AA151971:zo30b03.r1 *Homo sapiens* cDNA, 5 end | NC | 5 | 1.84 | P | P | P | P | A | 1.23 | 1.67 | 1.84 | 1.25 | 0.16 |
| X94216/FEATURE=cds/DEFINITION=HSVEGFC *H. sapiens* mRNA for VEGF-C protein | I | 5.4 | 1.8 | A | P | P | P | P | 3.41 | 2.03 | 4.39 | 7.18 | 7.43 |
| Cluster Incl. AL049389:*Homo sapiens* mRNA; cDNA DKFZp586O0118 (from clone DKFZp586O0118) | I | 2.3 | 1.74 | P | P | P | P | P | 8 | 7.04 | 6.58 | 6.44 | 6.74 |
| Cluster Incl. X76488:*H. sapiens* mRNA for lysosomal acid lipase | MI | 4.4 | 1.74 | P | P | P | P | P | 3 | 2.65 | 3.62 | 5.29 | 4.97 |
| Cluster Incl. J03191:Human profilin mRNA, complete cds | I | 2.4 | 1.57 | P | P | P | P | P | 4.83 | 4.59 | 5.29 | 4.85 | 4.25 |
| D13666/FEATURE=/DEFINITION=HUMOSF2OS *Homo sapiens* osf-2 mRNA for osteoblast specific factor 2 (OSF-2os), complete cds | I | 2.5 | 1.5 | A | P | P | P | P | 7.98 | 0.32 | 8.25 | 8.9 | 7.85 |
| Cluster Incl. AB002367:Human mRNA for KIAA0369 gene, complete cds | I | ~6.0 | 1.49 | P | M | P | P | P | 1.26 | 3.24 | 2.92 | 2.45 | 2.78 |
| Cluster Incl. W72186:zd69b10.s1 *Homo sapiens* cDNA, 3 end | I | 2.6 | 1.44 | P | P | P | P | P | 5.42 | 3.8 | 5.34 | 5.75 | 6.09 |
| Cluster Incl. AB003151:*Homo sapiens* DNA, chromosome 21q22.2, PAC clone 25P16 complete sequence, encoding carbonyl reductase and carbonyl reductase 3 (complete cds) | I | 5.2 | 1.44 | A | P | P | P | P | 1.65 | 1.41 | 3.87 | 3.53 | 3.05 |
| Cluster Incl. M94046:Human zinc finger protein (MAZ) mRNA | NC | 2.7 | 1.44 | P | P | P | P | P | 2.73 | 2.8 | 2.79 | 3.62 | 2.27 |
| Fk506-Binding Protein, Alt. Splice 2 | I | 3.4 | 1.43 | P | P | P | P | P | 4.97 | 3.51 | 5.46 | 6.99 | 5.22 |
| Cluster Incl. AI381790:te41h10.x1 *Homo sapiens* cDNA, 3 end | I | 2.8 | 1.42 | P | P | P | P | P | 3.69 | 3.72 | 5.56 | 5.15 | 6.65 |
| Cluster Incl. AL031670:dJ681N20.2 (ferritin, light polypeptide-like 1) | MI | 2.3 | 1.42 | A | A | P | P | A | 1.45 | 1.91 | 2.46 | 2.85 | 1.79 |
| Cluster Incl. AJ000534:*Homo sapiens* mRNA for epsilon-sarcoglycan | I | 2.8 | 1.39 | P | P | P | P | P | 5.57 | 2.55 | 6.73 | 7.14 | 6.69 |
| Cluster Incl. M32886:Human sorcin CP-22 mRNA, complete cds | I | 3.7 | 1.39 | P | P | P | P | P | 4.06 | 2.53 | 4.85 | 6.09 | 5.8 |
| Cluster Incl. L37033:Human FK-506 binding protein homologue (FKBP38) mRNA, complete cds | NC | ~5.7 | 1.34 | A | A | P | P | P | 0.74 | 0.32 | 0.9 | 2.41 | 2.06 |
| Cluster Incl. AL050287:*Homo sapiens* mRNA; cDNA DKFZp586C021 (from clone DKFZp586C021) | I | 3.1 | 1.32 | P | P | P | P | P | 3.97 | 3.08 | 4.59 | 4.78 | 5.39 |
| Cluster Incl. AF036956:*Homo sapiens* neuroblastoma apoptosis-related RNA binding protein (NAPOR-1) mRNA, complete cds | I | ~−6.6 | 1.32 | A | P | P | A | A | 1.7 | −0.2 | 3.63 | 1.19 | 1.72 |
| Cluster Incl. X95735:*Homo sapiens* mRNA for zyxin | MI | 2.8 | 1.31 | P | P | P | P | P | 2.74 | 3.19 | 3.58 | 4.21 | 3.82 |
| Cluster Incl. U87947:Human hematopoietic neural membrane protein (HNMP-1) mRNA, complete cds | I | 2.2 | 1.3 | P | P | P | P | P | 6.17 | 7.06 | 6.64 | 6.91 | 6.32 |
| Cluster Incl. AA977163:oq25a04.s1 *Homo sapiens* cDNA, 3 end | I | 1.9 | 1.29 | P | P | P | P | P | 5.92 | 6.9 | 7.43 | 7.84 | 6.22 |
| Cluster Incl. AF052389:*Homo sapiens* LIM domain binding protein (LDB1) mRNA, complete cds | I | ~5.8 | 1.28 | A | A | P | P | P | −0 | −0.1 | 3.08 | 4.09 | 5.38 |

TABLE 2B-continued

RESULT OF MICRO ARRAY ANALYSIS: NEGATIVE MARKERS
Negative markers: entries are ranked on sort score, the description column contains the Genbank Accession number and a short description of the protein encoded by it. The other column headers are explained at the beginning of table 1.

| Descriptions | Diff Call | P3-P0 Fold Change | P3-P0 Sort Score | Absolute call | | | | | Log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| Cluster Incl. AL022097:*Homo sapiens* DNA sequence from PAC 256G22 on chromosome 6p24.1-25.3. Contains a HNRNP Core Protein A1 LIKE pseudogene and an exon with similarity to yeast and fly phenylalanyl tRNA synthetase PHERS. Contains ESTs and GSSs | I | 2.2 | 1.27 | P | P | P | P | P | 7.94 | 7.53 | 7.94 | 8.23 | 7.68 |
| Cluster Incl. L41143:*Homo sapiens* expressed pseudo TCTA mRNA at t(1;3) translocation site, complete cds | MI | 4.1 | 1.26 | P | P | P | P | P | 2.4 | 1.64 | 3.63 | 4.6 | 3.63 |
| Calmodulin Type I | I | 2.3 | 1.24 | P | P | P | P | P | 6.35 | 6.33 | 6.48 | 7.04 | 6.7 |
| J04617/FEATURE=cds/DEFINITION=HUMEF1A Human elongation factor EF-1-alpha gene, complete cds | NC | 2.3 | 1.24 | A | A | P | P | A | 1.32 | 1.33 | 1.93 | 1.52 | 1.23 |
| Cluster Incl. J02854:Human 20-kDa myosin light chain (MLC-2) mRNA, complete cds | I | 2.2 | 1.23 | A | P | P | P | P | 4.64 | 1.21 | 4.86 | 4.81 | 3.94 |
| Cluster Incl. AI658639:tu06g05.x1 *Homo sapiens* cDNA, 3 end | I | 3 | 1.18 | P | P | P | P | P | 3.01 | 3 | 4.06 | 4.82 | 3.87 |
| Cluster Incl. AJ011981:*Homo sapiens* mRNA sequence | NC | 3.9 | 1.18 | A | A | P | M | A | 0.61 | 0.55 | 1.59 | 1.19 | 0.5 |
| M34539 Human FK506-binding protein (FKBP) mRNA, complete cds | I | 2.3 | 1.17 | P | P | P | P | P | 4.84 | 4.5 | 5.56 | 5.79 | 4.64 |
| Cluster Incl. U77643:*Homo sapiens* K12 protein precursor mRNA, complete cds | NC | ~5.6 | 1.17 | A | A | P | A | P | 1.3 | 1.01 | 1.99 | 2 | 3.53 |
| D28423/FEATURE=/DEFINITION=HUMPSF82 Human mRNA for pre-mRNA splicing factor SRp20, 5 UTR (sequence from the 5 cap to the start codon) | I | 2.7 | 1.16 | P | P | P | P | P | 6.28 | 7.16 | 6.11 | 7.43 | 6.48 |
| Cluster Incl. D38251:*Homo sapiens* mRNA for RPB5 (XAP4), complete cds | NC | 2.7 | 1.16 | P | P | P | P | P | 2.27 | 2.95 | 3.11 | 3.47 | 3.06 |
| Cluster Incl. U61374:Human novel protein with short consensus repeats of six cysteines mRNA, complete cds | I | 2.8 | 1.15 | A | P | P | P | P | 3.96 | 1.42 | 5 | 4.32 | 4.52 |
| Cluster Incl. AF010309:*Homo sapiens* Pig3 (PIG3) mRNA, complete cds | I | 4.5 | 1.15 | A | P | P | P | P | 3.84 | 1.62 | 3.88 | 4.51 | 4.77 |
| Cluster Incl. X98248:*H. sapiens* mRNA for sortilin | MI | 3.5 | 1.15 | A | P | P | P | P | 1.77 | 1.02 | 2.99 | 3.29 | 2.84 |
| L37882/FEATURE=/DEFINITION=HUMFRIZ Human frizzled gene product mRNA, complete cds | I | 5 | 1.14 | A | P | P | P | P | 1.53 | 0.38 | 2.73 | 3.86 | 4.54 |
| Cluster Incl. AF040963:*Homo sapiens* Mad4 homolog (Mad4) mRNA, complete cds | NC | ~5.6 | 1.14 | A | A | P | P | P | 1.13 | 0.38 | 1.43 | 2.33 | 1.86 |
| Cluster Incl. AF026692:*Homo sapiens* frizzled related protein frpHE mRNA, complete cds | I | 4.6 | 1.13 | P | P | P | P | P | 1.49 | 1.02 | 4.71 | 1.99 | 2.67 |
| Cluster Incl. Y11710:*H. sapiens* mRNA for extra-cellular matrix protein collagen type XIV, C-terminus | I | 3.9 | 1.12 | A | P | P | P | P | 2.21 | 0.49 | 3.68 | 6.25 | 7.29 |
| Cluster Incl. D86961:Human mRNA for KIAA0206 gene, partial cds | I | 2.3 | 1.08 | P | P | P | P | P | 6.34 | 6.5 | 6.72 | 5.78 | 4.78 |
| Cluster Incl. X96584:*H. sapiens* mRNA for NOV protein | I | 3.1 | 1.06 | A | P | P | A | A | 3.31 | 0.76 | 5.09 | 2.08 | 1.8 |
| Cluster Incl. AL080078:*Homo sapiens* mRNA; cDNA DKFZp564D1462 (from clone DKFZp564D1462) | NC | 4.5 | 1.06 | A | A | P | A | A | 1.78 | 1.91 | 3.53 | 1.68 | 1.33 |
| Cluster Incl. L17131:Human high mobility group protein (HMG-I(Y)) gene exons 1-8, complete cds | NC | 2.6 | 1.05 | P | P | P | P | P | 2.73 | 3.27 | 3.43 | 5.01 | 4.09 |
| L76200 Human guanylate kinase (GUK1) mRNA, complete cds | I | 2.2 | 1.04 | P | P | P | P | P | 4.96 | 5.23 | 5.69 | 5.97 | 5.26 |
| Cluster Incl. AF047473:*Homo sapiens* testis mitotic checkpoint BUB3 (BUB3) mRNA, complete cds | I | 3.4 | 1.04 | P | P | P | P | P | 5.11 | 6.24 | 5.15 | 6.63 | 5.74 |
| Cluster Incl. AA527880:nh86h10.s1 *Homo sapiens* cDNA, 3 end | I | 3.2 | 1.04 | P | P | P | P | P | 3.41 | 2.28 | 3.2 | 3.59 | 2.56 |
| Cluster Incl. Y08387:*H. sapiens* mRNA for mu-ARP2 protein | NC | 4.4 | 1.03 | A | A | P | A | A | 0.88 | 0.72 | 1.63 | 0.74 | 0.85 |
| Cluster Incl. U58516:Human breast epithelial antigen BA46 mRNA, complete cds | NC | 1.9 | 1.01 | P | P | P | P | P | 4 | 4.48 | 4.93 | 5.59 | 4.51 |
| Cluster Incl. J04182:*Homo sapiens* lysosomal membrane glycoprotein-1 (LAMP1) mRNA, complete cds | I | 2 | 1.01 | P | P | P | P | P | 3.5 | 3.98 | 4.14 | 4.22 | 3.44 |
| Cluster Incl. U68186:Human extracellular matrix protein 1 mRNA, complete cds | MI | 2.5 | 1.01 | A | P | P | P | P | 2.13 | 0.27 | 3.07 | 2.37 | 2.76 |

TABLE 2B-continued

RESULT OF MICRO ARRAY ANALYSIS: NEGATIVE MARKERS
Negative markers: entries are ranked on sort score, the description column contains the Genbank Accession number and a short description of the protein encoded by it. The other column headers are explained at the beginning of table 1.

| Descriptions | Diff Call | P3-P0 Fold Change | P3-P0 Sort Score | Absolute call | | | | | Log avg | | | | |
|---|---|---|---|---|---|---|---|---|---|---|---|---|---|
| | | | | FI | p0 | P3 | hpp3 | hpp10 | p0 | FI | P3 | hpp3 | hpp10 |
| M15205/Human thymidine kinase gene, complete cds, with clustered Alu repeats in the introns | NC | 4 | 1.01 | A | A | P | P | P | 1.49 | 0.06 | 1.77 | 5.2 | 3.11 |

EXAMPLE 11—VALIDATION OF CANDIDATE MARKERS

To separate the gene expression variability linked to the cartilage-forming ability from that due to general variability between samples, some individual marker genes that were differentially expressed according to the microarray were validated in a semi-quantitative RT-PCR approach comparing 4 independent chondrocytes samples at P0 to 4 other chondrocytes samples that had failed in the mouse assay at passage 3 to 7. The age of the donors ranged from 24 years to 65 years and was matched in the 2 groups compared. The primers and PCR conditions used are summarized in Table 3.

Figure 10:
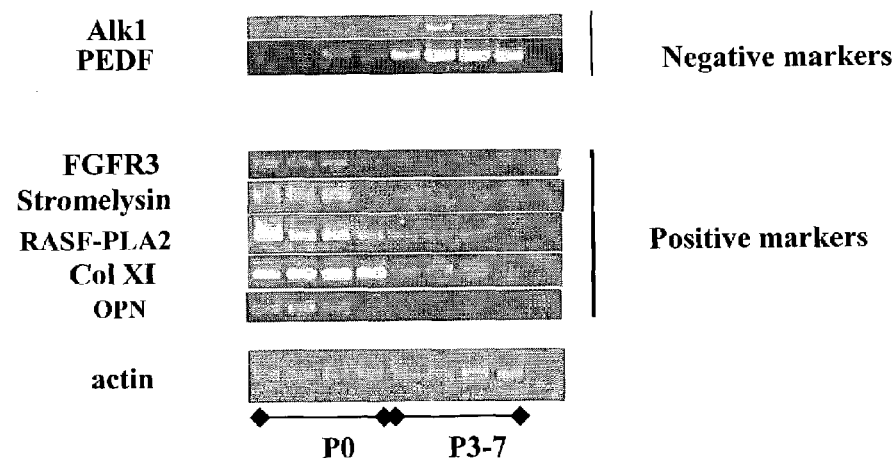
FIG. 10 shows an RT-PCR analysis of a representative number of markers selected from the pool of candidate markers at different passages of human chondrocytes.

A number of the markers disclosed in Tables 2A and 2B have been validated for their reproducibility in 4 samples of adult human articular chondrocytes at p0 (capable to form cartilage in vivo), versus 4 samples ranging from p3 to p4 (that had failed in the mouse assay for cartilage formation) from age-matched donors. The results are summarized in FIG. 10.

Stromelysin, RASF-A PLA2, alpha1 type 11 collagen, Fritz and OPN proved to be reproducible positive markers. Pigment epithelium-differentiation factor proved to be a reproducible negative marker.

TABLE 3

Accession number, description of the gene product and primer pairs used for RT PCR

| | |
|---|---|
| M76979 | *H. sapiens* pigment epithelium-differentiation factor (PEDF) mRNA, complete cds. |

TABLE 3-continued

Accession number, description of the gene product and primer pairs used for RT PCR

| | |
|---|---|
| Sense primer: | TTCAAGGGGCAGTGGGTAAC [SEQ ID NO:2] |
| Reverse primer: | TAAGGTGATAGTCCAGCGGG [SEQ ID NO:3] |
| M22430; J04704 | Human RASF-A PLA2 mRNA, complete cds. |
| Sense primer: | TCCCAACTCTGGAGTCCTCT [SEQ ID NO:4] |
| Reverse primer: | TGGTTAGGGTAGGGAGGGAG [SEQ ID NO:5] |
| X05232 | Human mRNA for stromelysin. |
| Sense primer: | CCAGCCAACTGTGATCCTGC [SEQ ID NO:6] |
| Reverse primer: | CTGGCTCCATGGAATTTCTC [SEQ ID NO:7] |
| J04177 | Human alpha-1 type XI collagen (COL11A1) mRNA |
| Sense primer: | GAGACTGGATTTCAAGGCAAG [SEQ ID NO:8] |
| Reverse primer: | TGAACTCCATCTCTCCCTGC [SEQ ID NO:9] |
| U91903 | Human Fritz mRNA, complete cds. |
| Sense primer: | TGTAAGTCTGTGTGCGAGCG [SEQ ID NO:10] |
| Reverse primer: | GATTTAGTTGCGTGCTTGCC [SEQ ID NO:11] |

The invention claimed is:

1. A method for providing an isolated or expanded cell population with in vivo chondrocyte phenotypic stability which comprises:
   (a) assaying said cell population for the expression of a positive marker or a negative marker; and
   (b) identifying and selecting said cell population expressing said positive marker or not expressing said negative marker as a cell population having in vivo chondrocyte phenotypic stability;

wherein the positive marker and negative markers are differentially expressed by a population of isolated or expanded cartilage cells, which when injected intramuscularly or subcutaneously in an animal are found to be capable of forming stable, non-vascularized cartilage in vivo, compared to a population of isolated or expanded cartilage cells which, when injected intramuscularly or subcutaneously in an animal, are found not to produce stable hyaline cartilage in vivo; the positive markers being positively associated to chondrocyte phenotypic stability and the negative markers being negatively associated with chondrocyte phenotypic stability.

2. The method of claim 1, wherein said positive marker is selected from expressed bone morphogenic protein-2 (BMP-2) or fibroblast growth factor receptor 3 (FGFR-3).

3. The method of claim 1, wherein said positive marker is selected from the group consisting of expressed stromelysin, rheumatoid arthritis synovial fluid phospholipase A2 (RASF-PLA2), collagen type 11 alpha 1 (Col XI), Fritz, and osteopontin (OPN).

4. The method of claim 1, wherein said positive markers are specific reporter constructs of expressed BMP-2, FGFR-3, stromelysin, RASF-PLA2, ColXI, Fritz and OPN.

5. The method of claim 1, wherein said negative marker is selected from expressed activin-like kinase-1 (ALK-1) and pigment epithelium derived factor (PEDF).

6. The method of claim 1, wherein said negative marker is a specific reporter construct of expressed ALK-1 or PEDF.

7. The method of claim 1, wherein the expression of said markers is detected by sets of DNA probes provided on DNA arrays or DNA chips for routine detection of chondrocyte stability, said DNA probes hybridizing to messenger RNA related to the expression of said positive and/or negative markers for chondrocyte stability.

8. The method of claim 1, which is a method for quality control of cells to be used for autologous cell transplantation.

9. The method of claim 1, wherein said identification is used as a tool to monitor passage by passage cell expansion of cells with chondrocyte phenotypic stability.

10. The method of claim 1 which comprises assaying the expression by said cell population of at least 2 of said positive and negative markers.

11. The method of claim 1, which comprises assaying the expression by said cell population of at least 6 of said positive and negative markers.

12. The method of claim 1, which comprises establishing that said cell population expresses a ratio of positive marker for chondrocyte phenotypic stability over negative marker for chondrocyte phenotypic stability which is greater than 1.

13. The method according to claim 12, wherein said ratio of positive marker for chondrocyte phenotypic stability over negative marker for chondrocyte phenotypic stability is greater than 2.

14. A therapeutic composition for humans including cells identified according to claim 1, optionally further including at least a pharmaceutically acceptable carrier and/or a growth factor.

15. The composition of claim 14, said composition including a pharmaceutically acceptable carrier.

16. The composition of claim 14, said composition including a growth factor.

17. The composition of claim 14, said composition including a pharmaceutically acceptable carrier and a growth factor.

* * * * *

SEQUENCE LISTING

```
<160> NUMBER OF SEQ ID NOS: 11

<210> SEQ ID NO 1
<211> LENGTH: 40
<212> TYPE: PRT
<213> ORGANISM: Homo sapiens

<400> SEQUENCE: 1

Thr Gly Leu Val Pro Ser Glu Arg Val Leu Val Gly Pro Gln Arg Leu
1               5                   10                  15

Gln Val Leu Asn Ala Ser His Glu Asp Ser Gly Ala Tyr Ser Cys Arg
            20                  25                  30

Gln Arg Leu Thr Gln Arg Val Leu
        35                  40
```

```
<210> SEQ ID NO 2
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Pigment epithelium-differentiation factor
      sense primer

<400> SEQUENCE: 2
ttcaaggggc agtgggtaac                                              20

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Pigment epithelium-differentiation factor
      reverse primer

<400> SEQUENCE: 3
taaggtgata gtccagcggg                                              20

<210> SEQ ID NO 4
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: RASF-A PLA2      sense primer

<400> SEQUENCE: 4
tcccaactct ggagtcctct                                              20

<210> SEQ ID NO 5
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: RASF-A PLA2      reverse primer

<400> SEQUENCE: 5
tggttagggt agggagggag                                              20

<210> SEQ ID NO 6
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: stromelysin    sense primer

<400> SEQUENCE: 6
ccagccaact gtgatcctgc                                              20

<210> SEQ ID NO 7
<211> LENGTH: 20
<212> TYPE: DNA
<213> ORGANISM: Homo sapiens
```

```
<220> FEATURE:
<221> NAME/KEY: misc_feature
<222> LOCATION: (1)..(20)
<223> OTHER INFORMATION: stromelysin   reverse primer

<400> SEQUENCE: 7
ctggctccat ggaatttctc                                                20

<210> SEQ ID NO 8
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: alpha 1 type XI collagen   sense primer

<400> SEQUENCE: 8
gagactggat ttcaaggcaa g                                              21

<210> SEQ ID NO 9
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: alpha-1 type XI collagen reverse primer

<400> SEQUENCE: 9
tgaactccat ctctccctgc                                                20

<210> SEQ ID NO 10
<211> LENGTH: 20
<212> TYPE: DNA
<213> ORGANISM: homo sapiens
<220> FEATURE:
<221> NAME/KEY: misc_feature
<222> LOCATION: (1)..(20)
<223> OTHER INFORMATION: Fritz   sense prime

<400> SEQUENCE: 10
tgtaagtctg tgtgcgagcg                                                20

<210> SEQ ID NO 11
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Fritz   reverse primer

<400> SEQUENCE: 11
gatttagttg cgtgcttgcc                                                20
```